US009424722B2

(12) United States Patent
Adrezin et al.

(10) Patent No.: US 9,424,722 B2
(45) Date of Patent: Aug. 23, 2016

(54) SMART MEMORY MATERIAL LOCK DEVICES

(71) Applicant: Unlimited Liability, LLC, Mineola, NY (US)

(72) Inventors: Ronald S. Adrezin, East Lyme, CT (US); Robert Dinan, Simsbury, CT (US); Steven S. Legum, Mineola, NY (US); John Nordyke, West Hartfort, CT (US)

(73) Assignee: UNLIMITED LIABILITY, LLC, Mineola, NY (US)

( * ) Notice: Subject to any disclaimer, the term of this patent is extended or adjusted under 35 U.S.C. 154(b) by 279 days.

(21) Appl. No.: 14/120,261

(22) Filed: May 14, 2014

(65) Prior Publication Data

US 2015/0332567 A1 Nov. 19, 2015

(51) Int. Cl.
*G08B 13/14* (2006.01)
*G08B 13/08* (2006.01)
(Continued)

(52) U.S. Cl.
CPC ............ *G08B 13/08* (2013.01); *E05B 47/0009* (2013.01); *E05B 65/52* (2013.01); *G08B 21/0288* (2013.01)

(58) Field of Classification Search
CPC ..... G06F 1/163; G06F 1/1626; G06F 1/1628; G06F 1/1656; G06F 1/1637; G06F 1/1662; G06F 1/166; G06F 2200/1633; G06F 1/1616; G06F 1/1624; G06F 1/1669; G06F 1/182; G06F 1/16; G06F 1/1605; G06F 1/1632; G06F 1/1635; G06F 1/1652
USPC ........................ 340/5.64, 5.61, 539.15, 568.1
See application file for complete search history.

(56) References Cited

U.S. PATENT DOCUMENTS 4,189,712 A * 2/1980 Lemelson ............. E05B 49/006 235/382
4,354,189 A * 10/1982 Lemelson ............. E05B 49/006 340/10.33

(Continued)

FOREIGN PATENT DOCUMENTS

CN 100547213 10/2009
EP 0 213 873 B1 3/1987

(Continued)

OTHER PUBLICATIONS

"GPS Monitoring system helps ensure offender compliance", THOMASNET, Aug. 30, 2006.

(Continued)

*Primary Examiner* — Jennifer Mehmood
*Assistant Examiner* — Rufus Point
(74) *Attorney, Agent, or Firm* — Foley & Lardner LLP

(57) ABSTRACT

Tracking device embodiments, comprising: portable housing with a locking mechanism; band latched about a wrist; tampering detection device to detect tampering with the band, comprising: power source; latch configured to latch one end of the band within the housing; a shape memory material component connected to the latch; an electrical circuit for controlling the power source to heat the shape memory material component to cause the shape memory material component to change from a first length/shape to a second length/shape during supply of power to perform a locking function; a timer; two-way network communication device; a tracking element; tampering signal generation circuit. In embodiments, a tamper resistant container cap, comprises: cap housing releasably lockable to an open end of a container and a locking mechanism using a shape memory material component.

17 Claims, 21 Drawing Sheets

(51) Int. Cl.

| | |
|---|---|
| ***E05B 47/00*** | (2006.01) |
| ***E05B 65/52*** | (2006.01) |
| *G08B 21/02* | (2006.01) |

(56) References Cited

U.S. PATENT DOCUMENTS

| | | | | |
|---|---|---|---|---|
| 5,349,345 | A | 9/1994 | Vanderschel | |
| 5,774,059 | A | 6/1998 | Henry et al. | |
| 5,955,960 | A | 9/1999 | Monnier | |
| 6,163,737 | A | 12/2000 | Fedor et al. | |
| 6,362,778 | B2 | 3/2002 | Neher | |
| 6,382,416 | B1 | 5/2002 | Gainey | |
| 6,388,612 | B1 | 5/2002 | Neher | |
| 6,695,207 | B1 * | 2/2004 | Norris, Jr. | B60R 25/23 235/380 |
| D623,965 | S | 9/2010 | Sullivan et al. | |
| 8,035,479 | B2 | 10/2011 | Tran | |
| 8,047,031 | B2 | 11/2011 | Bellamy et al. | |
| 8,827,331 | B2 * | 9/2014 | Corcoran | G11B 33/125 269/903 |
| 8,912,901 | B2 * | 12/2014 | Hoeth | H04Q 9/00 340/540 |
| 8,974,349 | B2 * | 3/2015 | Weast | G06F 1/163 482/1 |
| 9,129,503 | B2 * | 9/2015 | Borlenghi | G08B 21/0269 |
| 2001/0055243 | A1 | 12/2001 | Haywood | |
| 2006/0267760 | A1 | 11/2006 | Shecter | |
| 2007/0125816 | A1 * | 6/2007 | Myers | A44C 5/0007 224/221 |
| 2009/0013736 | A1 | 1/2009 | Voosen | |
| 2009/0024062 | A1 * | 1/2009 | Einarsson | A41D 13/1281 600/595 |
| 2010/0137679 | A1 * | 6/2010 | Lashinski | A61B 17/0401 600/37 |
| 2010/0176146 | A1 | 7/2010 | Ben-Dor | |
| 2013/0113612 | A1 * | 5/2013 | Curen | G08C 17/02 340/12.5 |
| 2013/0119096 | A1 * | 5/2013 | Morgan | A45F 3/005 224/148.1 |
| 2014/0163664 | A1 * | 6/2014 | Goldsmith | A61B 17/00491 623/1.11 |
| 2014/0275850 | A1 * | 9/2014 | Venkatraman | A61B 5/0002 600/301 |
| 2015/0185764 | A1 * | 7/2015 | Magi | G06F 1/163 361/679.03 |

FOREIGN PATENT DOCUMENTS

| | | |
|---|---|---|
| EP | 0 787 216 | 8/1997 |
| EP | 0 963 497 | 12/1999 |
| EP | 1 532 888 | 5/2005 |
| EP | 2 473 419 | 7/2012 |
| EP | 2 609 268 | 7/2013 |
| WO | WO-99/60235 | 11/1999 |
| WO | WO-99/66373 | 12/1999 |
| WO | WO-03/088190 | 10/2003 |
| WO | WO-2004/001235 | 12/2003 |
| WO | WO-2004/039204 | 5/2004 |
| WO | WO-2009/029370 | 3/2009 |
| WO | WO-2011/059712 | 5/2011 |
| WO | WO-2013/086310 | 6/2013 |

OTHER PUBLICATIONS

"PhilaU ID Alum Wins Microsoft Healthcare Innovation Award", Philadelphia University Industrial Design, Feb. 25, 2014.

Bar-Cohen, "Electro-active polymers: current capabilities and challenges", Paper 4695-02, Proceedings of the SPIE Smart Structures and Materials Symposium, EAPAD Conference, San Diego, CA , Mar. 18-21, 2002.

GPS Monitoring Solutions monitors Juveniles (http://www.gpsmonitoring.com/Tracking-of-Juveniles.html), Jan. 3, 2014.

GPS Tracking Device for Kids, Child GPS, Jan. 3, 2014, pp. 1-2 (www.brickhousesecurity.com).

GPS, iSecureTrac Systems & Services, Jan. 3, 2014, pp. 1-3.

Pickens, "Building Prisons Without Walls Using GPS Devices 545", Aug. 31, 2010.

Revolutionary Wristwatch—Cell Phone with GPS-911 Panic Button System, LEO, Sep. 21, 2010.

* cited by examiner

FIG. 10
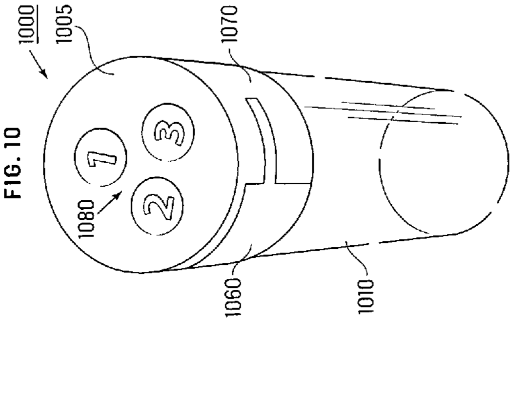
FIG. 11
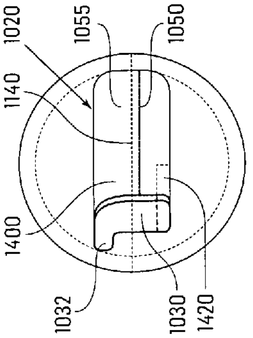
FIG. 12
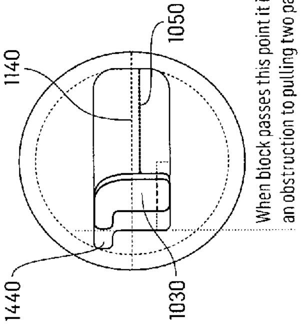
FIG. 13
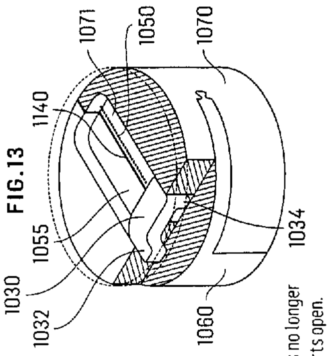
FIG. 14
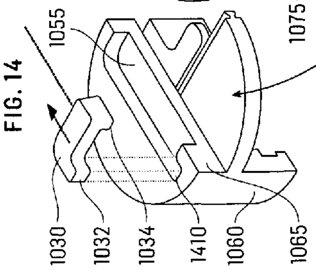
FIG. 15
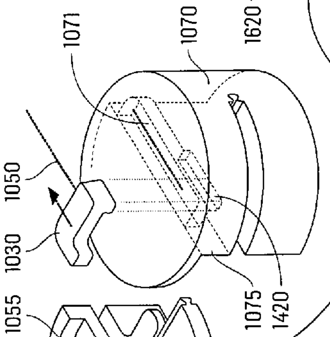
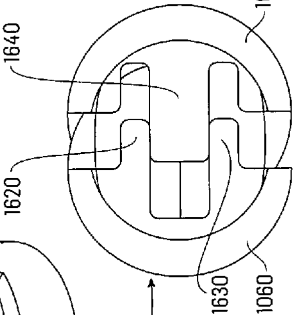
FIG. 16A
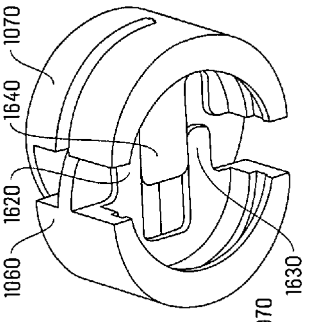
FIG. 16B
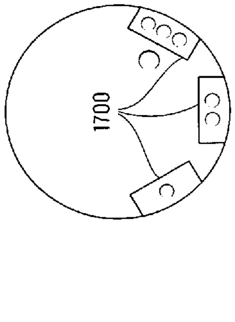
FIG. 17
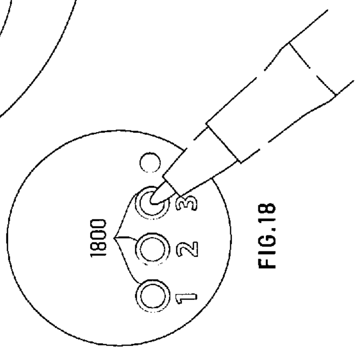
FIG. 18

FIG.19
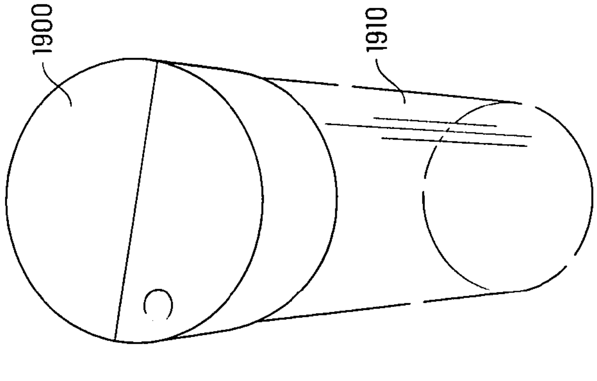
FIG. 20
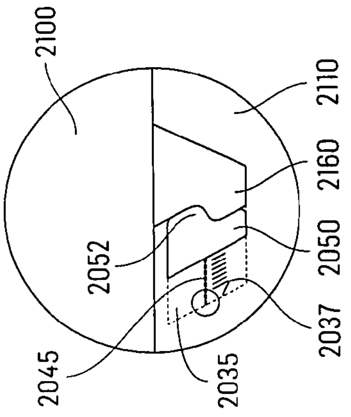
FIG. 21
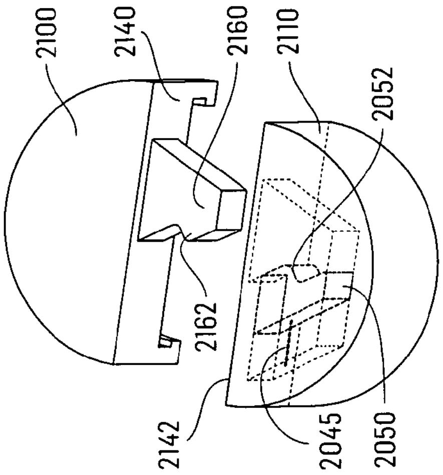
FIG. 22
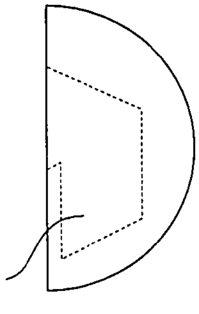
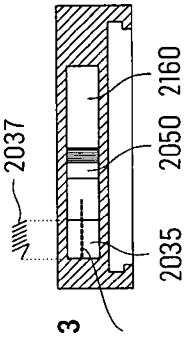
FIG. 23
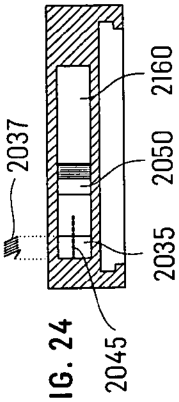
FIG. 24

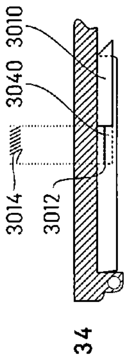
FIG. 34
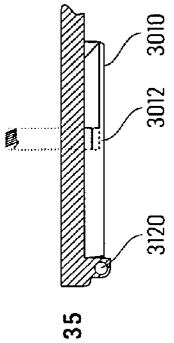
FIG. 35
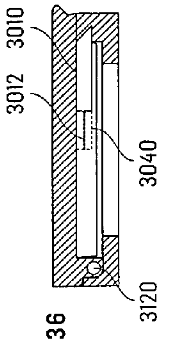
FIG. 36
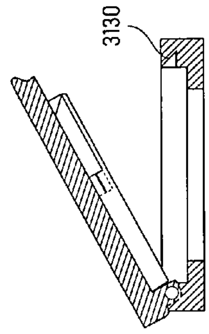
FIG. 37
FIG. 31
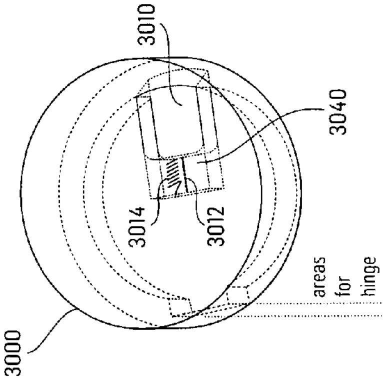
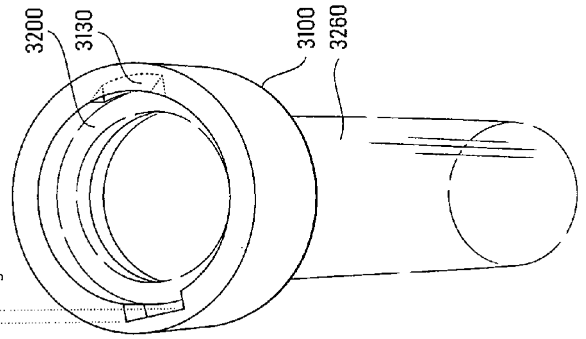
FIG. 33
FIG. 30
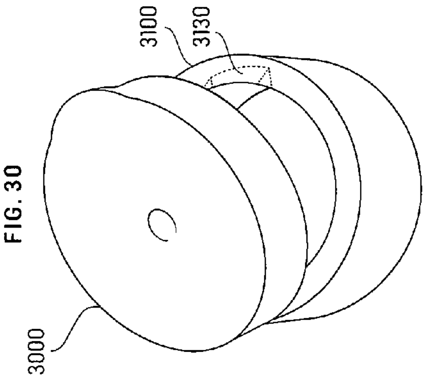
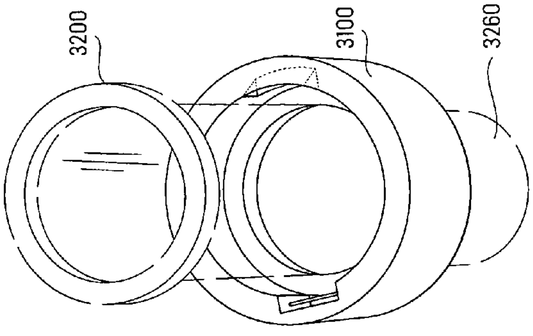
FIG. 32

FIG. 52
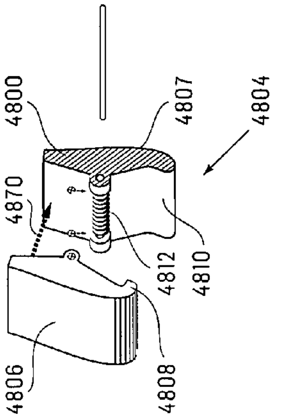
FIG. 50
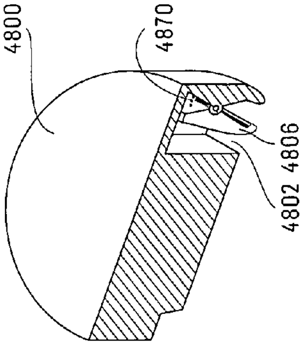
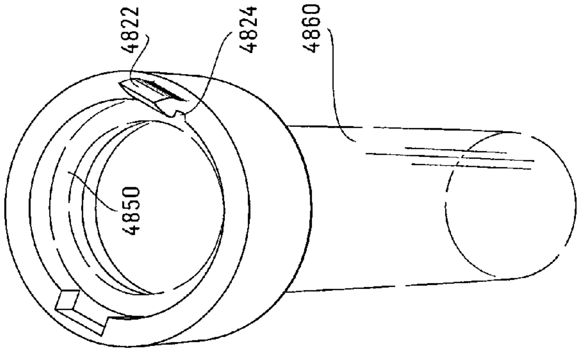
FIG. 51
FIG. 48
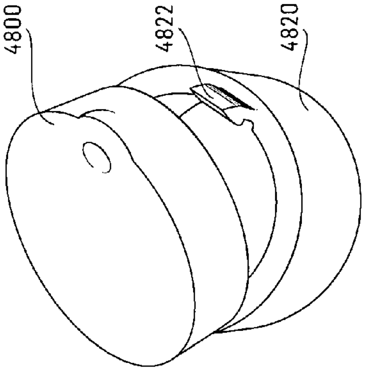
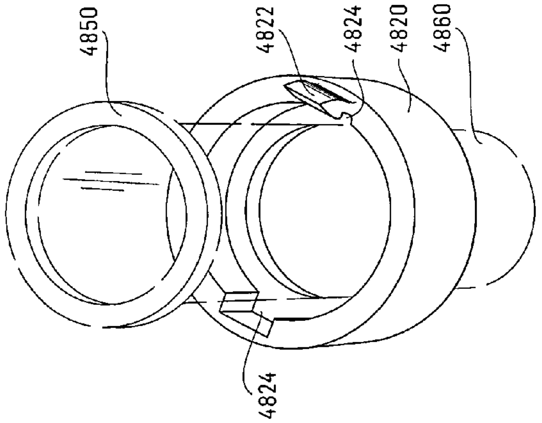
FIG. 49

FIG. 91
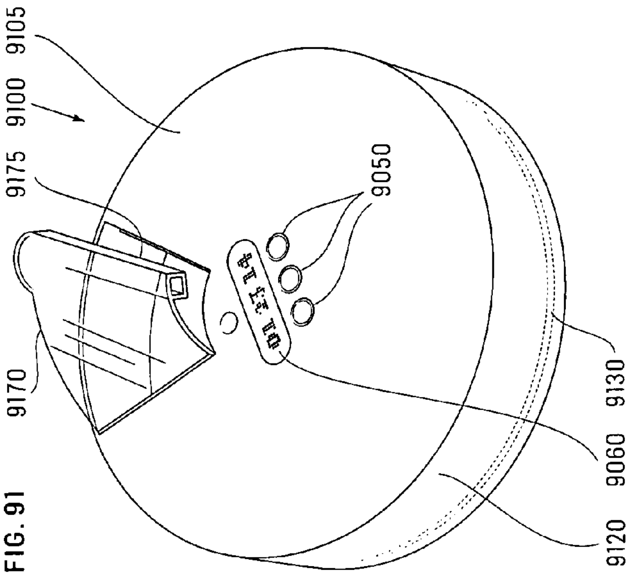
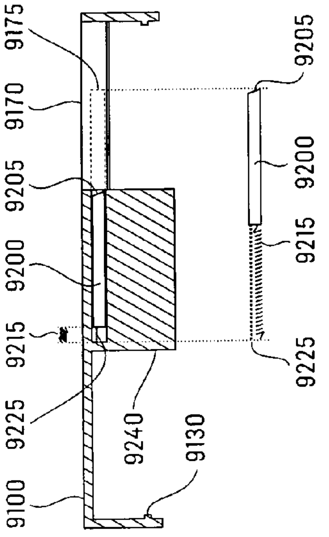
FIG. 92A
FIG. 92B
FIG. 90
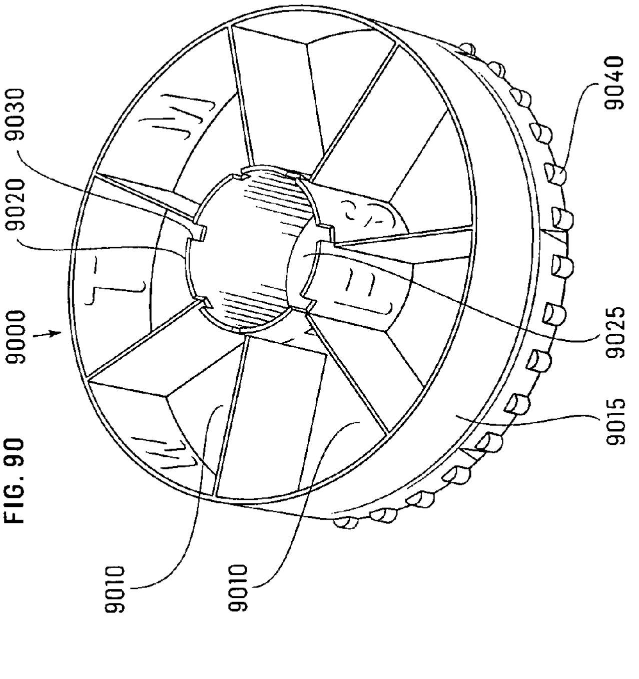

SMART MEMORY MATERIAL LOCK DEVICES

BACKGROUND

The present application relates generally to the field of tracking devices and container caps.

Problems arises in tracking devices for individuals, e.g., children, couriers, retirement home individuals. Likewise, problems have arisen in controlling access to medicine containers and other types of containers.

SUMMARY OF THE INVENTION

Embodiments of a tracking device are disclosed, comprising: a portable housing with a locking mechanism; a band in cooperation with the portable housing and configured to be latched about a wrist or ankle of a person; a tampering detection device configured in relation to the housing and/or the band to detect tampering with the band or unauthorized release. In embodiments, the locking mechanism comprises a power source; a latch configured to latch at least one end of the band within the housing; a shape memory material component connected to the latch; an electrical circuit for controlling the power source to heat the shape memory material component to cause the shape memory material component to change from a first length and/or first shape to a second length and/or second shape during supply of power; wherein when the shape memory material component has the first length and/or shape, the latch prevents release of the one end of the band, and when the shape memory material component has the second length and/or shape, the latch is moved to allow release of the one end of the band. In embodiments, the electrical circuit may be configured to control heating of the shape memory material component based on one or more criteria. In embodiments, a timer component may be associated with the electrical circuit to cause supply of the power for a predetermined period of time when the electrical circuit component is triggered to heat the shape memory material component. In embodiments, a two-way network communication device disposed in cooperation with the portable housing. In embodiments, a tracking element may be provided for facilitating location determination and transmission of a location signal. In embodiments, a tampering signal generation circuit may be provided that is configured to generate a tampering signal for transmission via the two-way communication device when tampering is detected by the tampering detection device.

In embodiments, the shape memory material component may comprise a shape memory material alloy, or an electroactive polymer, or a twisted carbon nanotube.

In embodiments, the shape memory material component may comprise a shape memory material wire.

In embodiments, the tracking device may further comprise an audible alarm device to generate an audible alarm signal when tampering is detected by the tampering detection device.

In embodiments, the tracking device may further comprise a panic button on the portable housing connected to the two-way communication device to generate a panic signal for transmission via the two-way communication device.

In embodiments, the tracking device may further comprise a stress detector disposed in the portable housing and/or the band and configured: to measure one or more biological indicators, and to generate a signal for transmission providing a stress alert and location data via the two-way communication device when stress based on measurements of one or more of the one or more biological indicators is determined.

In embodiments, the latch may comprise an interference block.

In embodiments, the latch may comprise an interference block that pivots on an axis between a first position that functions to lock the one end of the band within the housing, and a second position that allows the band to be released from the portable housing.

In embodiments, the electrical logic component may be configured to limit a level of the electrical current supplied to the shape memory material component to a predetermined current range.

In embodiments, when the electrical circuit supplies current from the electrical current source to the shape memory material component, the shape memory material component may change from the first length and the first shape to the second length and the second shape.

In embodiments, the latch may comprise a lever attached directly or indirectly to an interference block, and when the shape memory material component takes the second length and/or shape, the lever may be configured to move the interference block out of interference with the band so that the band may be released from the portable housing.

In embodiments, the latch may comprise an interference block configured to slide between a first interfering position and a second non-interfering position when the length and/or the shape of the shape memory material component changes.

In embodiments, the tracking device may further comprise a spring positioned to hold the interference block in the first interfering position.

In embodiments, the power source may comprise an electrical current source selected from the group of a battery, a kinetic charger, and an induction device.

In embodiments, the tracking element may comprise one or more selected from the group of a GPS circuit and a cellular telephone circuit.

In embodiments, the invention may comprise a tamper resistant container cap, comprising: a cap housing releasably lockable to an open end of a container and a locking mechanism disposed in the cap housing. In embodiments, the locking mechanism may comprise: an interference block moveable between a first interfering position and a second non-interfering position; a power source; a shape memory material component connected to the interference block; and an electrical circuit for controlling the power source to heat the shape memory material component to cause the shape memory material component to change from a first length and/or first shape to a second length and/or second shape during supply of power; wherein the shape memory material component is disposed in relation to the interference block so that when the shape memory material component has the first length and/or shape, the interference block is disposed to prevent removal of the cap housing from the open end of the container, and when the shape memory material component has the second length and/or shape, the interference block allows the cap housing to be removed from the open end of the container; wherein the electrical circuit is configured to control heating of the shape memory material component based on one or more criteria. In embodiments, the electrical circuit may comprise a timer component associated with the electrical circuit to cause supply of the power for a predetermined period of time when the electrical circuit component is triggered to heat the shape memory material component;

In embodiments, the cap housing may have a first portion and a second portion that are separated when the shape memory material component has the second length and/or shape so that the interference block is in the second position that allows the cap housing to be removed from the open end of the container.

In embodiments, the first portion and the second portion may have one or more registration fingers that are in adjacency and parallel and are slidably configured so that the one or more fingers of the first portion move away from the one or more fingers of the second portion when the interference block moves into the second non-interfering position.

In embodiments, the interference block may be configured to slide between the first interfering position and the second non-interfering position when the shape memory material length and/or shape changes.

In embodiments, the cap housing may comprise a first portion and a second portion, with a first lateral track formed in the first portion of the cap housing with a slot at one end thereof, and a second lateral track formed in the second portion of the cap housing, with the second lateral track in parallel and adjacency to the first lateral track, and the interference block may comprise a lateral projection at one end thereof that slides within the first lateral track and the fits within the slot of the first lateral track when the shape-memory material component has the first length and/or shape, and the interference block may comprise a downward projection at another end thereof that slides within the second lateral track.

In embodiments, the cap housing may comprise a key pad for controlling the electrical logic component supplying electrical current from the electrical current source to the shape memory material component to cause the shape memory material component to change between the first length and/or shape and the second length and/or shape.

In embodiments, the electrical circuit may comprise logic to allow the interference block to take the second non-interfering position only during specified hours of a day or only a specified number of times per day or only one or more specified days of the week.

In embodiments, the container cap may further comprise: a network communication device comprising a receiver disposed in the portable housing for receiving control signals from a communication network to control the electrical circuit to supply electrical current from the electrical current source to the shape memory material component to cause the shape memory material component to change between the first length and/or shape and the second length and/or shape, and the electrical circuit may comprise logic to control supply of the electrical current from the electrical current source to the shape memory material component based at least in part on the control signals.

In embodiments, the network communication device may comprise a cellular telephone circuit or a transceiver.

In embodiments, the container cap may further comprise a network communication device comprising a receiver and a transmitter disposed in the portable housing for receiving and sending voice signals over a network.

In embodiments, the electrical circuit may comprise logic for generating for data transmission on removal of the cap housing from the open end of the container, and the network communication device may be configured to transmit the data on the removal of the cap housing from the open end of the container.

In embodiments, the cap housing may further comprise an electronic display screen, wherein the electrical circuit may further comprise an electronic memory, and the electrical circuit may be configured to record data on removal of the cap housing from the open end of the container in the electronic memory and display data based on the removal data on the electronic display screen.

In embodiments, the container cap may further comprise a spring positioned to hold the interference block in the first interfering position.

In embodiments, the power source may comprise an electrical current source selected from the group of a battery, a kinetic charger, and an induction device.

In embodiments, the electrical circuit may be configured to limit a level of the electrical current supplied to the shape memory material component to a predetermined electrical current range.

In embodiments, the container cap may further comprise: a network communication device disposed in the cap housing; and a tracking element comprising one or more selected from the group of a GPS circuit and a cellular telephone circuit for location determination and transmission of location data over a communications network via the network communication device.

In embodiments, the shape-memory material component may be a shape-memory alloy component, an electroactive polymer, or a twisted carbon nanotube.

In embodiments, the cap housing may comprise a first portion and a second portion, with opposing parallel surfaces, with a projection extending from the parallel surface of the first portion, with a side extension that extends substantially parallel to the parallel surface from the projection, the second portion may comprise a recess in which the projection may fit when the first and second portions are fitted together, the recess in the second portion may comprise an interference block with a side projection, wherein the interference block is laterally slidable within the recess in a direction that is parallel to the parallel surface, so that the side projection of the interference block fits in registration with the side extension of the projection of the first portion within the recess when the shape-memory material component has the first length and/or shape so that the interference block is in a first interfering position.

In embodiments, the cap housing may comprise a first portion and a second portion, with opposing parallel surfaces, interference block may comprise two pieces on a same plane positioned to be rotatable around a track within the first portion, the second portion may comprise a track on the same plane as the track in the first portion and positioned to receive at least a portion of the two pieces therein when the pieces are rotated away from each other; the shape memory material component may be connected to opposing sides of the two pieces, wherein when the shape memory material component has the first length and/or shape, the two pieces may be rotated apart into the track in the second portion to thereby impede removal of the cap housing from the open end of the container, and when the shape memory material component has the second length and/or shape, the two pieces are not rotated into the second portion thereby not interfering with removal of the cap housing from the open end of the container.

In embodiments, each of the two pieces comprises a fractional portion of a disk that is positioned to slide on the track in the first portion.

In embodiments, the container cap may comprise a recess disposed to extend from inside the container cap to an opening in a side of the container cap, wherein the interference block may be positioned within the recess, and slidable within the recess to project through the opening into a recess on a side of the container, to thereby be in an interfering position, wherein the shape memory material component is connected at one end thereof within the recess in the container cap, and connected at another end thereof to the interference block, wherein when the shape memory material component has the first length and/or shape, an end of the interference block may be extended into the recess into the container, and when the shape memory material component has the second length and/or shape, the interference block is entirely within the recess in the container cap and in the non-interfering position.

In embodiments, the container cap may further comprise a hinge connecting one end of the container cap to an edge of the opening in the container.

In embodiments, the interference block may comprise two pieces, with each piece comprising at least one end, and the shape memory material component may be positioned between the two pieces, so that when the shape memory material component has the first length and/or shape, the at least one end for each of the pieces is extended into a respective recess in a side of the open end of the container, and when the shape memory material component has the second length and/or shape, the at least one end for each of the pieces is not extended into its respective recess in the side of the open end of the container.

In embodiments, the cap housing may comprise a first portion and a second portion, the interference block may comprise two pieces on a same plane positioned to be rotatable around a track within the first portion, wherein each of the two pieces comprises a circumferential projection at one end thereof, with the projections positioned to oppose each other and to form a boundary of an opening defined within the two pieces adjacent the one end, the second portion may comprise a track on the same plane as the track in the first portion and positioned to receive at least a portion of the two pieces therein that have the circumferential projections thereon, the second portion may comprise a projection positioned thereon to fit within the opening defined within the two pieces, the shape memory material component may be connected to opposing sides of the two pieces, wherein when the shape memory material component has the first length and/or shape, the two pieces may be rotated so that the circumferential projections are in adjacency or touch to thereby trap the projection on the second portion with the opening to thereby impede removal of the cap housing from the open end of the container, and when the shape memory material component has the second length and/or shape, the two pieces are rotated to move the circumferential projections away from each other to no longer trap the projection on the second portion and allow removal of the cap housing from the open end of the container.

In embodiments, each of the two pieces may comprise a fractional portion of a disk that is positioned to slide on the track in the first portion.

In embodiments, the two pieces may be biased so that the circumferential projections are in adjacency or touch to thereby trap the projection on the second portion with the opening.

In embodiments, the cap housing may comprise a first portion and a second portion, the interference block may comprise a first clip piece with an end thereof biased toward a second clip piece to form a clip connected to the first portion, the second portion may comprise a knob extending from a surface of the second portion, with the knob having indents formed below a top portion of the knob, and with the knob positioned in alignment with the clip so that clip fits around the knob when in a locked position and prevents the first portion from being separated from the second portion, and the shape memory material component may be connected between the first clip piece and the second piece so that when the shape memory material component has the first length and/or shape, the interference block is disposed around the knob in the indents to prevent separation of the first portion from the second portion, and when the shape memory material component has the second length and/or shape, the interference block allows separation of the first portion from the second portion.

In embodiments, the container cap may further comprise a spring for biasing the end of the clip piece toward the end of a wall of the first portion.

In embodiments, the end of the second clip piece may comprise a wall of the first portion.

In embodiments, the clip may be positioned perpendicular and toward the opening of the container.

In embodiments, the clip may be positioned in parallel to the opening of the container.

In embodiments, the cap housing may comprise a first portion and a second portion with opposing parallel surfaces, the interference block may comprise a first clip piece with an end thereof biased toward an end of a second clip piece to form a clip connected to the first portion, with the clip positioned within a recess formed in the parallel surface of the first portion, but extending partially from the surface of the parallel surface of the first portion, the second portion may comprise a projection extending across a recess formed in the parallel surface of the second portion formed, the clip may be positioned so that the end of the first clip piece and the end of the second clip piece extend into the recess on either side of the projection to fit around and behind the projection in the second portion when in a locked position and prevent the first portion from being separated from the second portion, and the shape memory material component may be connected between the first clip piece and the second piece so that when the shape memory material component has the first length and/or shape, the ends of the first and second clip pieces extend around and behind the projection in the second portion to prevent separation of the first portion from the second portion, and when the shape memory material component has the second length and/or shape, the ends of the first and second clip pieces are moved apart to allow separation of the first portion from the second portion.

In embodiments, the cap housing may comprise a hinge at a first side thereof to hinge the cap housing to a first side of the open end of the container, and the interference block may be positioned at a second side of the cap housing that is opposite to the side with the hinge.

In embodiments, the interference block may comprise a clip, a second side of the open end of the container opposite to the first end may comprise a knob extending from a surface of the second side of the open end of the container, with the knob having at least one indent formed below a top portion of the knob, and with the knob positioned in alignment with the clip so that clip fits around the knob into the indent when in a locked position and prevents the cap housing from being separated from the open end of the container, and the shape memory material component may be connected within the clip so that when the shape memory material component has the first length and/or shape, the interference block is disposed to around the knob in the at least one indent to prevent separation of the cap housing from the open end of the container, and when the shape memory material component has the second length and/or shape, the interference block allows separation of the cap housing from the open end of the container.

In embodiments, the interference block may be slidable between a first locking position and a second unlocked position, a second side of the open end of the container opposite to the first end may comprise a knob extending from a surface of the second side of the open end of the container, with the knob having at least one indent formed below a top portion of the knob, and with the knob positioned so that the interference block may be slid so that a portion thereof fits in registration with the indent in the knob when in a locked position to prevent the container cap from being separated from the second side of the container, and the shape memory material component may be connected to one end of the interference block so that when the shape memory material component has the first length and/or shape, the interference block is positioned to fit in registration with the indent in the knob for the locked position to prevent separation of the cap housing from the open end of the container, and when the shape memory material component has the second length and/or shape, the interference block is no longer in registration with the indent in the knob thereby allowing separation of the cap housing from the open end of the container.

In embodiments, the interference block may be biased into the locked position.

BRIEF DESCRIPTION OF THE DRAWINGS

The accompanying drawings, which are included to provide further understanding of the invention, are incorporated in and constitute a part of this specification, illustrate embodiments of the present disclosure and together with the detailed description serve to explain the principles of the present disclosure. No attempt is made to show structural details of the present disclosure in more detail than may be necessary for a fundamental understanding of the present disclosure and the various ways in which it may be practiced.

FIG. 10 is a perspective view of an embodiment of container cap.

FIG. 11 is a top view of the embodiment of FIG. 11 with the interference block in an interfering position.

FIG. 12 is a perspective view of the embodiment of FIG. 11 with the interference block in a non-interfering position.

FIG. 13 is a perspective view of the embodiment of FIG. 11.

FIG. 14 is a perspective view one portion of the embodiment of FIG. 11 with the interference block in exploded view.

FIG. 15 is a perspective view a second portion of the embodiment of FIG. 11 with the interference block in exploded view.

FIG. 16A is a bottom view of the embodiment of FIG. 11.

FIG. 16B is a perspective view from the bottom of the embodiment of FIG. 11.

FIG. 17 is a top view of an embodiment of a keypad for a container.

FIG. 18 is a top view of another embodiment of a keypad for a container.

FIG. 19 is a perspective view of an embodiment of a container and container cap.

FIG. 20 is a top view of another embodiment of a container cap.

FIG. 21 is a perspective view of the embodiment of the container cap of FIG. 20.

FIG. 22 is a top view of the embodiment of the container cap of FIG. 20 with a recess show in hidden lines.

FIG. 23 is a cross-section view of the second portion with the interference block in an interfering position.

FIG. 24 is a cross-section view of the second portion with the interference block in a non-interfering position.

FIG. 30 is a perspective view of a further embodiment of the container cap and a top of a container.

FIG. 31 is a perspective view of the container cap embodiment of FIG. 30 showing an interference block.

FIG. 32 is a perspective view of the container cap embodiment of FIG. 30 shown in exploded view.

FIG. 33 is a perspective view of the container for the embodiment of FIG. 30.

FIG. 34 is a cross-section side view of the container cap for the embodiment of FIG. 30 with the interference block in an interfering position.

FIG. 35 is a cross-section side view of the container cap for the embodiment of FIG. 30 with the interference block in a non-interfering position.

FIG. 36 is a cross-section side view of the container cap and container for the embodiment of FIG. 30 with the interference block in an interfering position.

FIG. 37 is a cross-section side view of the container cap for the embodiment of FIG. 30 with the interference block in a non-interfering position.

FIG. 48 is a perspective view of embodiments of a container cap consistent with the invention.

FIG. 49 is a perspective view of embodiments of a bottom portion of the container cap of FIG. 48 with an exploded view of a lip of a container illustrated.

FIG. 50 is a perspective cross-sectional view of embodiments of a top portion of the container cap of FIG. 48.

FIG. 51 is a perspective view of the bottom portion of the container cap of FIG. 48.

FIG. 52 is a perspective view of embodiments of a locking mechanism that may be used with the container cap of Fig: 48.

FIG. 90 is a perspective view of embodiments of the container consistent with the invention, with a lid removed.

FIG. 91 is a perspective view of embodiments of the container consistent with the invention, with a lid on the container.

FIG. 92A is a cross-section side view of the lid with an interference block that may be used to implement a locking mechanism for the invention.

FIG. 92B is a side view of the interference block of FIG. 92A shown in a locked position.

DETAILED DESCRIPTION OF EMBODIMENTS

Before turning to the figures, which illustrate the exemplary embodiments in detail, it should be understood that the present disclosure is not limited to the details or methodology set forth in the description or illustrated in the figures. It should also be understood that the terminology is for the purpose of description only and should not be regarded as limiting. An effort has been made to use the same or like reference numbers throughout the drawings to refer to the same or like parts.

Figures 1, 2, 3, 4, 5, 6A, 6B, 7, 8, 9:
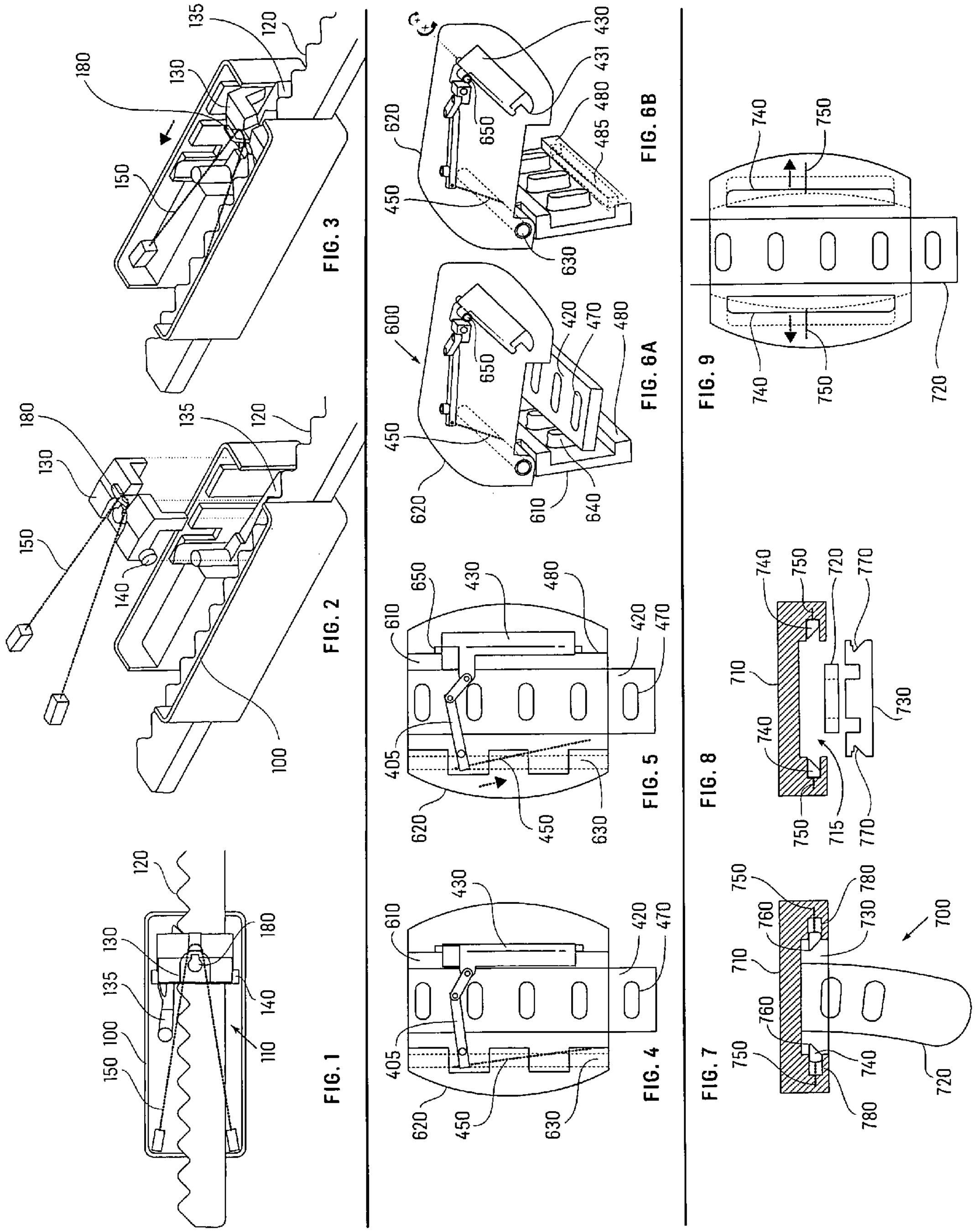
FIG. 1 is a top view schematic diagram of an embodiment of the tracker device invention with an embodiment of the latch in a locked position.
FIG. 2 is a perspective view of the embodiment shown in FIG. 1 of the tracker device invention with the latch separated in the view.
FIG. 3 is a perspective view of the embodiment shown in FIG. 1 of the tracker device invention with the embodiment of the latch in an unlocked position.
FIG. 4 is a top view schematic diagram of an embodiment of the tracker device invention with a second embodiment of the latch in a locked position.
FIG. 5 is a top view of the embodiment shown in FIG. 4 of the tracker device invention with the second embodiment of the latch in an unlocked position.
FIG. 6A is a perspective view of the embodiment shown in FIG. 4 of the tracker device invention with the second embodiment of the latch in an unlocked position.
FIG. 6B is a perspective view of the embodiment shown in FIG. 4 of the tracker device invention showing a longitudinal recess 485.
FIG. 7 is a side cross-sectional view of an embodiment of the tracker device of the invention.
FIG. 8 is a side cross-sectional view of an embodiment of the tracker device of the invention with the lower portion 730 and the band 720 shown as released.
FIG. 9 is a top view of an embodiment of the tracker device of the invention.

Referring to FIGS. 1-3, a first embodiment of the invention is disclosed. Therein a portable housing 100 with a locking mechanism 110 is illustrated in cooperation with a band 120 for a tracking device. The band may be of a length sufficient to be latched about a wrist or ankle or other appendage of a person. In embodiments, the locking mechanism 110 may comprise a power source (an embodiment of a current source is shown as element 4112 in FIGS. 38 and 39) controlled by an electrical circuit. The locking mechanism 110 may further comprise a latch 130 configured to latch at least one end of the band within the housing. In embodiments, the latch may comprise an interference block 130 that may be slid or pivoted or otherwise moved between an interfering position that prevents removal of the band and a non-interfering position where the band may be removed. In the embodiments of FIGS. 1-3, the interference block 130 may be pivoted on an axis 140 between a first position that functions to lock the one end of the band 120 within the housing 100, and a second position that allows the band to be released from the portable housing. In FIG. 2, the interference block 130 is shown in the down first position that interferes with and prevents the band 120 from being released and slid out of the portable housing 100. In FIG. 3, the interference block 130 is shown pivoted up to allow the band 120 to be released from the housing 100. In embodiments, a pawl 135 with a tooth at one end may be positioned to fit into grooves on the side of the band 120. In embodiments, the pawl 135 may be spring loaded or otherwise biased to pivot the pawl so that the tooth at the end fits into one of the grooves on the side of the band. When the interference block 130 is pivoted into the down or interfering position, legs of the interference block are moved into adjacency with a side of the pawl, thereby preventing the tooth from being retracted from the groove in the side of the band. When the interference block is in the up non-interfering position, the tooth may be retracted from the groove.

A control mechanism is provide to move the interference block 130 between the interfering position that prevents removal of the band 120 and the non-interfering position. For the embodiments of FIGS. 1-3, the control mechanism may be configured to pivot the interference block 130 up and/or down based on received electronic instructions. In embodiments, the control mechanism may comprise a shape memory material component 150 connected to the latch or interference block 130. In the embodiment shown in FIG. 1, the shape-memory material component 150 may be anchored to at least one point or area within the portable housing 100 and connected to the interference block 130. In the embodiments of FIGS. 1-3, the shape memory material component 150 is shown anchored at each end to an internal wall of the portable housing. In embodiments, the shape-memory material component may comprise a wire 150 that extends to and is looped around a projection 180 on the interference block 130. When the shape memory material component 150 has the first length shown in FIG. 1, the latch prevents release of the one end of the band. When the shape memory material component 150 has the second length as shown in FIG. 3, the latch is moved, e.g., the interference block 130 is pivoted up, to allow release of the one end of the band 120.

In embodiments, the shape memory material may comprise shape memory alloys such as nickel-titanium and/or copper-aluminum-nickel, shape-memory polymer, and vanadium dioxide. For design details for use of shape memory materials, see "TECHNICAL CHARACTERISTICS OF FLEXINOL" by Dynalloy, Inc., Tustin, Calif., (www.dynalloy.com), provided in an information disclosure statement and hereby incorporated by reference. In embodiments, the shape memory material may comprise an electroactive polymer. In embodiments, the shape memory material may be constructed from twisted carbon nanotubes. In this respect, so the reference "Electro-active polymers: current capabilities and challenges," by Yoseph Bar-Cohen, Paper 4695-02, Proceedings of the SPIE Smart Structures and Materials Symposium, EAPAD Conference, San Diego, Calif., Mar. 18-21, 2002. Each of these materials substantial changes length and/or shape when heated, for example, by electrical current. In embodiments, the shape memory material heated by light directed thereon.

In embodiments, the shape memory material component may take a variety of different shapes and configurations. In embodiments, the shape memory material component may comprise a rectangular block. In embodiments, the shape memory material component may comprise a band. In embodiments, the shape memory material component may comprise a tubular element. In embodiments, the shape memory material component may be formed into the shape of a spring (coil, torsional, leaf, etc.) to hold an interference block in place.

When electrical current is run through the material formed as a spring, or light applied, or it is heated by another means, then its shape or length may be changed (e.g., to lengthen or contract it). In embodiments, this spring configuration may save one component The invention is not intended to be limited by the shape that the shape-memory material component can take or by the means used for heating the material.

In embodiments, the control mechanism may alternatively comprise a micro-motor (not shown) cooperating with the interference block 130 to move the interference block into and out of interference with the band 130 when current at a desired level is applied. In embodiments, the micro-motor may pivot the interference block. In embodiments, the micromotor may slide the interference block, rather than pivot the interference block.

In embodiments, the power source may comprise an electrical current source such as a battery and/or kinetic charger, and/or an induction element.

Figure 38:
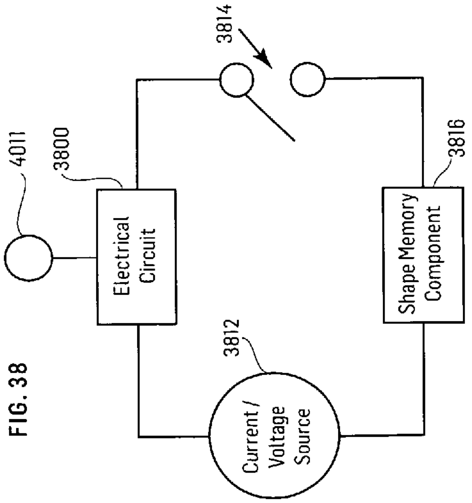
FIG. 38 is a schematic block diagram of an embodiment of a circuit diagram that may be used to implement embodiments using a shape memory material component.

FIG. 38 illustrates embodiments with an electrical current source 3812, a switching device 3814 that controls supply of electrical current from the electrical current source 3812 to a shape memory material component 3816 to cause the shape memory material component to change at least from the first length and/or shape to the second length and/or shape during supply of the power, e.g., electrical current, and an electrical circuit 3800 for controlling the switching device 3814. In embodiments, the switching device 3814 may comprise an FET transistor switch. In embodiments, the electrical circuit 3800 may control the switching device 3814 based on one or more parameters. For example, the electrical circuit 3800 may control the switching device 3814 in accordance with a control signal received via a wireless or wired receiver in the electrical circuit 3800. In embodiments, there may also be a local release mechanism that generates the control signal to allow release of the band.

Figure 39:
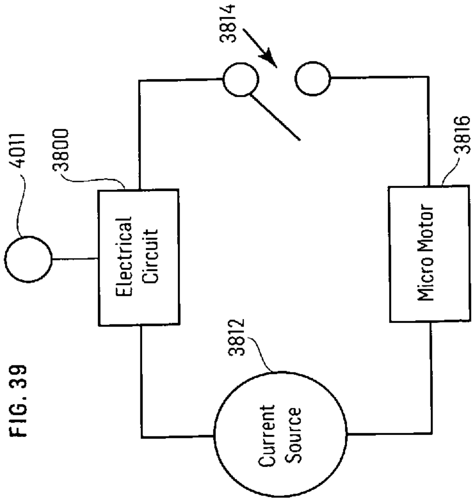
FIG. 39 is a schematic block diagram of an embodiment of a circuit diagram that may be used to implement embodiments using a micro-motor.

A comparable circuit is shown in FIG. 39, but using a micro-motor 3816 rather than the shape memory component.

Figure 40:
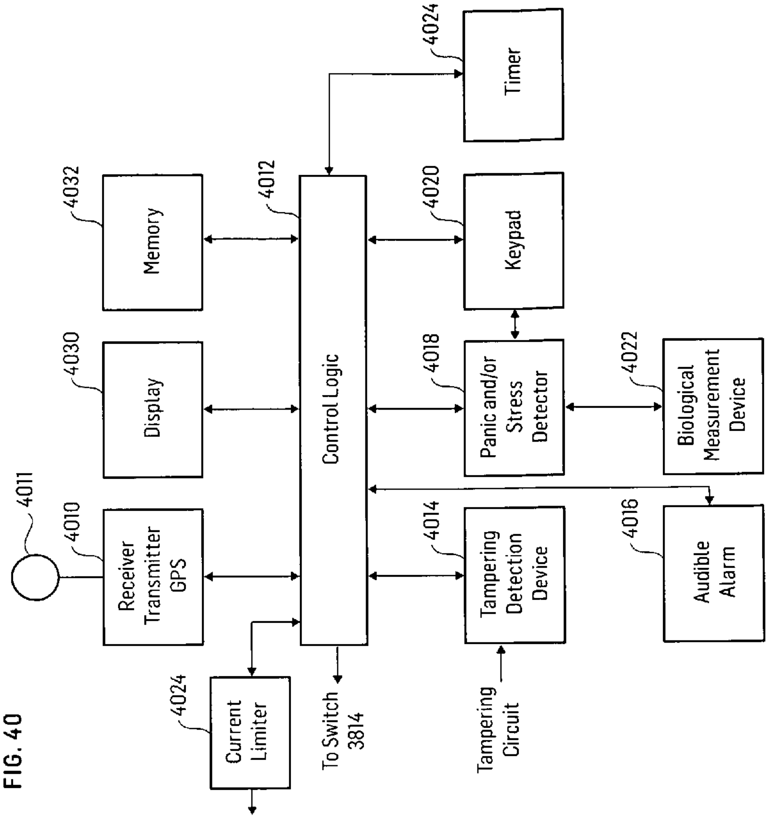
FIG. 40 is a schematic block diagram of an embodiment of an electrical circuit that may be used to implement the invention.

Embodiments of an electrical circuit 3800 consistent with the invention are illustrated in more detail in FIG. 40. In embodiments, the electrical circuit may comprise a control logic which controls the current source and the transmission of signals, based on logic criteria. In embodiments, the electrical circuit 3800 may comprise a two-way communication network device 4010 (shown in FIG. 40) disposed in cooperation with the portable housing. In embodiments, the two-way communication network device 4010 may comprise a cellphone. In embodiments, the two-way communication network device 4010 may comprise a transceiver. In embodiments, the two-way communication network device may comprise an antenna 4011.

In embodiments, the electrical circuit may further comprise a tracking element (also represented as element 4010 in FIG. 40) disposed in the portable housing for facilitating location determination and transmission of a location signal. In embodiments, the tracking element may comprise a GPS receiver circuit. In embodiments, the tracking element may comprise a cellular receiver circuit.

In embodiments, the electrical circuit may further comprise a tampering detection device 4014 (shown in FIG. 40) configured in relation to the portable housing 100 and/or the band 120 to detect tampering with the band or unauthorized release. In embodiments, the tampering detection device 4014 may comprise a tampering circuit including one or more lead wires running the length of the band 120, which would trigger generation of a tampering signal when the tampering circuit is broken. In embodiments, the generation of the tampering signal may trigger transmission of an alert signal via the two-way communication device 4010.

In embodiments, the band 120 may comprise a thin metal band, e.g., an aluminum band. In embodiments a Kevlar or equivalent wrap may be wrapped around the thin metal band. In embodiments, dikes on the wrap may be disposed perpendicular to the width dimension of the band. It has been determined that in some embodiments, the wrap may absorb and redirect cutting pressure, thereby significantly impeding cutting. In embodiments, one or more lead wires may be placed on the inside of the band next to the wearer's wrist or ankle.

In embodiments, the electrical circuit may further comprise an audible alarm device 4016 to detect the tampering, and via the control logic 4102, to have generated an audible alarm signal when tampering is detected by the tampering detection device. In embodiments, the audible alarm device may be disposed in the portable housing and may be connected to a circuit containing the lead wires in the band.

In embodiments, the electrical circuit 3800 may further comprise a panic device 4018 on the portable housing connected via the control logic 4012 to the two-way communication device 4010 to generate a panic signal for transmission via the two-way communication device. In embodiments, the panic device may comprise one or more buttons in a keypad disposed on a surface of the portable housing 100. In embodiments, when one or more panic buttons are pushed, or pushed in a predetermined sequence, the panic and/or stress detector 4018 will cause, via the control logic 4012, an alarm circuit 4016 to generate an audible alarm and/or to generate a panic signal that is transmitted via the two-way communication network device 4010. In embodiments, this panic signal that is transmitted may comprise location data obtained from the tracking device in block 4010, e.g., the GPS circuit, or the cellular receiver circuit.

In embodiments, the electrical circuit may further comprise a stress detector 4018 disposed in the portable housing and/or on the band 120 to measure one or more biological indicators via a biological measurement device 4022, and to generate a signal to the control logic 4012 to cause generation and transmission of a stress alert and location data via the two-way communication device 4010 when stress based on measurements of one or more of the one or more biological measurement devices 4022 is determined. In embodiments, the biological measurement device 4022 may comprise a heart rate and/or blood pressure monitor and logic which generates a signal when the heart rate and/or blood pressure exceed one or more thresholds.

In embodiments, the electrical circuit may further comprise a current limiter 4024 configured to limit a level of the electrical current supplied to the shape memory material component to a predetermined current range. In embodiments, this predetermined current range may be determined empirically.

In embodiments, when the electrical circuit supplies current from the electrical current source to the shape memory material component, the shape memory material component may be configured to change from a first length and/or a first shape to a second length and/or a second shape.

In embodiments, the electrical circuit may further comprise a timer 4024 associated with the control logic 4012 to cause supply of the power, e.g., electrical current for a predetermined period of time when the electrical circuit is triggered, e.g., when the switching device 3814 is in the closed position to supply electrical current to the shape memory material component. The timer 4024 may be set to a time, e.g., 3 or 4 or 5 seconds, empirically determined to be sufficient for the person to release the band 120 from the portable housing 100 when the latch 130 is moved to its second release or non-interfering position. In embodiments, the timer circuit may comprise a Pulse Width Modulation driver circuit, as opposed to a power source and resistor. The Pulse Width Modulation circuit has the advantage of using less power. In some embodiments, this timing function may be accomplished in the current source. In some embodiments, the timer may be implemented by a limit switch. When the shape memory material component is heated and changes to a new position, the power shuts off. If shape memory material component starts to cool too fast and the circuit is still telling it to be activated, the limit switch will depress and the power will be reinstated. In embodiments, the limit switch removes and applies power based on size/shape. If the shape memory material starts to cool, its shape/size will change and the current will flow again. In some embodiments, depending on the diameter of the shape memory material component, it may take a few seconds or more to cool and therefore whenever the unlock button or an unlock signal is received, these few seconds may be available before the configuration relocks. Thus, in embodiments, the timer may not be necessary.

In further embodiments illustrated in FIGS. 4-6, a portable housing may comprise a clam shell design 600 as illustrated in FIG. 6, with a bottom portion 610 for holding a band 420, and a pivotable top portion 620, which pivots on a longitudinal pin 630. FIGS. 4 and 5 are top horizontal cross-section views of the embodiment with the top portion 620 pivoted down or closed. The cross-section of FIGS. 4 and 5 is taken below a main section of the top portion so that latch levers 405, to be discussed below, are visible. FIG. 6 is a perspective view with the clam shell top portion pivoted up or open. In embodiments, the bottom portion may comprise one or more projections 640 that rise from an inner surface of the bottom portion 610. In embodiments, the band 420 may comprise one or more holes 470 therethrough to fit in registration with the one or more projections 640 to hold the band in place within the portable housing. The band 420 may be released when the top portion 620 is pivoted up or open so that the band 420 may be lifted out of registration with the one or more projections 640. Note that terms "top" and "bottom" are used for convenience of description and are not intended to be limiting. In embodiments the top portion and bottom portion may be reversed, e.g., the portion 610 with the projections 640 may be on top.

In embodiments for FIGS. 4-6, a latch for locking the band 420 within the housing may comprise one or more levers 405 attached to the top portion 620 of the portable housing. The one or more levers 405 may be connected directly or indirectly to an interference block 430 disposed in the top portion 620 of the portable housing 600. In embodiments, the interference block 430 may be in the form of a hook or other similar design to hook around an side 480 of the bottom portion 610 of the portable housing when in a locking position. In embodiments, a longitudinal recess 485 may be formed in the side 480 for an edge 431 of the interference block 430 to fit within. The longitudinal recess 485 is best seen as the dashed lines in FIG. 6B.

In embodiments, a shape memory material component 450 may be connected to the one or more levers 405. When the shape memory material component 450 takes a first length and/or shape as shown in FIG. 4, the one or more levers 405 are pulled to hold the hook end of the interference block 430 around the side 480 of the bottom portion 610 of the portable housing into the recess 485 so that the band 420 may not be released from the portable housing 400. When the shape memory material component 450 takes a second length (shown in FIGS. 6A and 6B) and/or shape, the one or more levers 405 are pulled to pivot the interference block 430 about an axis 650 out of interference with the band 420 so that the band 420 may be released from the portable housing 400. In embodiments, the shape memory material component 450 may be in the form of a wire.

Note that in embodiments, the shape memory material component may comprise a rectangular block. In embodiments, the shape memory material component may comprise a band. In embodiments, the shape memory material component may comprise a tubular element. The invention is not intended to be limited by the shape that the shape-memory material component can take.

In further embodiments illustrated in FIGS. 7-9, the portable housing may comprise a top portion 710 for receiving a band 720, and a bottom portion 730, that in embodiments may be fully or partially removable. In embodiments, the top portion 710 may comprise a recess 715 in which the bottom portion 730 may fit within. FIGS. 7 and 8 are vertical cross-section views of the portable housing 700. FIG. 7 illustrates the band 720 held in position by the bottom portion 730 that is latched to the top portion 710. FIG. 8 illustrates the band 720 released and the bottom portion 730 removed. Note that terms "top" and "bottom" are used for convenience of description and are not intended to be limiting. In embodiments the upper portion and bottom portion may be reversed, e.g., the portion 730 may be on top.

In embodiments, a latch for embodiments may comprise one or more slidable interference blocks 740 connected at one end thereof to a shape memory material component 750. In embodiments, the interference blocks 740 may each comprise a projection 760 at one end thereof. In embodiments, the shape memory material component 750 may be in the form of a wire. However, as noted above the shape memory material component may take a variety of shapes and configurations and a variety of connection points to the housing and the interference block. The invention is not intended to be limited by the shape that the shape-memory material component can take.

In embodiments, the one or more interference blocks 740 may be configured to slide within a recess 780 in the top portion 710 between a first interfering position and a second non-interfering position when the length of a shape memory material component 750 changes, to thereby allow release of the band 720.

In embodiments, the lower portion 730 may include one or more indents 770 disposed on respective sides thereof, with a size so that the projection 760 of the interference block 740 may fit in registration therewith to prevent the lower portion 730 from being released from the top portion 710 when the shape memory material component 750 has a first length and/or shape. When the shape memory material component 750 has a second length and/or shape, the one or more interference blocks 740 are slide into the respective recesses 780, to move the projection 760 of the interference blocks 740 out of the indents 770 and allow the bottom portion 730 to be removed or released. In embodiments, the projection 760 of the interference block may be beveled to permit the lower portion 730 to be pushed or pivoted into the recess 715 in the top portion 710 to lock the band 720 within the housing 700.

In embodiments, the tracking device of FIGS. 7-9 may further comprise a spring (not shown) or other biasing device positioned within the recess 780 between a portion of the interference block and an internal wall of the recess 780 to hold or maintain the interference block 740 in the first interfering position.

In a yet further embodiment, one or more pivoted arms may be positioned so that one end thereof fits in registration with a respective recess formed in a side of the band. In embodiments, each of the one or more pivoted arms may be pivoted between an interfering position where its respective one end fits in registration with the recess in the band, and a non-interfering position where the one end is pivoted out of the recess in the band. The pivoting may be under control of a shape memory material component or a micro-motor as described in other embodiments. In embodiments, the pivoted arms may be spring loaded or otherwise biased into the interfering position.

In embodiments, the interference block may comprise two pieces positioned within the bottom portion 730, with each piece comprising at least one projection, and the shape memory material component may be positioned between the two pieces, so that when the shape memory material component has the first length and/or shape, the at least one projection for each of the pieces is extended into a respective recess in a side of the open end of the container, and when the shape memory material component has the second length and/or shape, the at least one projection for each of the pieces is not extended into its respective recess in the side of the open end of the container.

Referring to FIGS. 10-18, embodiments of a tamper resistant container cap embodiment 1000 of the invention are illustrated. In embodiments, the tamper resistant container cap may comprise a housing 1005 configured to be releasably lockable to an open end of a container 1010 (shown in FIG. 10). In embodiments, the tamper resistant container cap 1000 may comprise a locking mechanism 1020 disposed within the cap housing 1005 for locking together two or more portions of the cap housing 1005 so that they cannot be separated and the container cap removed from the container 1010. In embodiments, the locking mechanism 1020 may comprise an interference block 1030 moveable between a first interfering position shown in FIGS. 11, 13 and 14, and a second non-interfering position shown in FIGS. 12 and 15. In embodiments, the container cap housing 1000 may be rotated without interference, when the interference block 1030 is in the second position.

In embodiment shown in FIGS. 10-18, the container cap 1000 may be configured in two pieces that may be fully or partially separated when the interference block 1030 is in the second position. In embodiments, the cap housing of the container cap 1000 may comprise a first portion 1060 and a second portion 1070 that may be separated when the interference block is in the second position to allow the cap housing to be the removed from the open end of the container.

In embodiments, the first portion 1060 and the second portion 1070 may have opposing faces or sides 1065 and 1075. In embodiments, the first portion 1060 may comprise a recessed track 1055 positioned along and in parallel to the face 1065. The second portion 1070 may comprise a a first recessed track 1071 and a second recessed track 1420 running in parallel and in adjacency to the track 1055. In embodiments, the interference block 1030 may be slidable along the recessed tracks 1055 and 1071. In the embodiments of FIGS. 10-18, the interference block 1030 may comprise a lateral projection or finger 1032 at one end thereof, and a downward projection 1034 disposed at another end thereof. In embodiments, the interference block 1030 may be slidable in the recessed track 1055 formed in the first portion 1060, and the lateral projection or finger 1032 may be positioned on the interference block 1030 to fit in registration with a slot 1410 formed in the first portion 1060 at one end of the recessed track 1055.

The downward projection 1034 at the another end of the interference block 1030, is configured to fit in a track 1420 set laterally in the second portion 1070 and running in parallel with the face or plane 1075 of the second portion 1070. In embodiments, the interference block 1030, is slidable within the track 1420 of the second portion 1070, but is not removable therefrom.

In embodiments of the operation, when the lateral projection or finger 1032 is in registration with the slot 1410, the interference block 1030 prevents the first portion 1060 from being pull apart or separated from the second portion 1070. When the interference block 1030 has been slid along the track 1055 to a position so that the lateral projection or finger 1032 is out of the slot 1410, the first portion 1060 and the second portion 1070 may be separated.

Accordingly, in embodiments, the container cap housing 1000 may have a first portion 1060 and a second portion 1070, with a first lateral recessed track 1055 formed in the first portion of the cap housing, with a slot 1410 at one end of the recessed track 1055, and a second lateral recessed track 1420 formed in the second portion 1070 of the cap housing, with the second lateral recessed track in parallel to the first lateral track 1055. As noted, the interference block 1030 may further comprise a lateral projection 1032 at one end thereof that slides within the first lateral recessed track 1055 and the fits within the slot 1410 of the first lateral track 1055 when the shape memory material component has the first length, and the interference block may comprise a downward projection 1034 at another end thereof that slides within the second lateral recessed track 1420 to prevent removal of the interference block from the second portion 1070.

In embodiments, the first portion 1060 and the second portion 1070 may have one or more registration fingers 1620, 1630, and 1640 that are in adjacency and parallel and are slidably configured so that the one or more fingers 1620 and 1630 of the first portion 1060 move away from the one or more fingers 1640 of the second portion 1070 when the interference block 1030 moves into the second non-interfering position.

In embodiments, a control mechanism may be configured to slide or pivot the interference block 1030 into or out of the interference position based on received electronic instructions. In embodiments, the control mechanism may comprise a shape-memory material component 1050 connected to the interference block 1030. In the embodiment shown in FIGS. 10-18, the shape-memory material component may be positioned within the recessed track 1055 and may comprise a wire 1050 that is anchored at one end of the recessed track 1055, and extends to and is connected to an end or a surface of the interference block 1030. In embodiments, the shape memory material may take the shape of a rectangular block or tube or rod, that changes length and/or shape when energized by the electrical current. As noted, the invention is not intended to be limited by the shape that the shape-memory material component can take. In embodiments, the shape memory material may comprise shape-memory alloys such as nickel-titanium and/or copper-aluminum-nickel, shape-memory polymer, and vanadium dioxide.

In embodiments, the container cap may further comprise a spring or other biasing device (not shown) positioned in one of the recessed tracks 1055, 1420, to hold the interference block 1030 in the first interfering position.

When the shape memory material component 1050 has the first length and/or shape shown in FIGS. 11, 13 and 14, the interference block 1030 is in an interfering position and prevents turning of the cap to access the container. When the shape memory material component 1050 has the second length and/or shape as shown in FIGS. 11 and 15, the interference block 1030 is slid or otherwise moved within the recessed track 1055 to the second position to allow separation of the first and second portions 1060 and 1070 to allow removal, e.g., twisting of the cap, to release the cap from the container. Thus, in embodiments, the shape memory material component is disposed in relation to the interference block 1030 so that when the shape memory material component has the first length, the interference block is disposed to prevent removal of the cap housing from the open end of the container, and when the shape memory material component has the second length, the interference block allows the cap housing 1000 to be removed from the open end of the container 1010.

In embodiments, the locking mechanism 1020 may further comprise an electrical current source 3812 (shown in FIG. 38) and an electrical circuit 3800 to control the current source to supply electrical current from the electrical current source to the shape memory material component to cause the shape memory material component to change at least from the first length and/or shape to the second length and/or shape during supply of the power, e.g., electrical current. In embodiments, the electrical current source 3812 may comprise a battery and/or kinetic charger, and/or an induction element.

In embodiments, the electrical circuit 3800 may be configured to control supply of power, e.g., electrical current from the current source 3812, to heat the shape memory material component based on one or more criteria. In embodiments, one of the one or more criteria used by the electrical circuit to control supply of electrical current from the current source to the shape memory material component may be implemented by the control logic of FIG. 40 to allow the interference block 1030 to take the second non-interfering position only during specified hours of a day, or only a specified number of times per day, or only one or more specified days of the week, or only when a signal is received from a communications network, or based on a manual input.

In embodiments, the electrical circuit 3800 may comprise a timer circuit 4024 as shown in FIG. 40 to cause when triggered, supply of the electrical current for a predetermined period of time to the shape memory material component.

In embodiments, the container cap may further comprise a network communication device 4010 comprising a receiver disposed in the portable housing for receiving control signals from a network to control the electrical circuit 3800 to supply electrical current from the electrical current source 3812 to the shape memory material component 3816 to cause the shape memory material component to change between the first length and/or shape and the second length and/or shape. As noted, the electrical circuit 3800 may further comprise logic 4012 to control supply of the power, e.g., electrical current from the electrical current source, to heat the shape memory material component based at least in part on the control signals. In embodiments, the network communication device 4010 may comprise a cellular telephone circuit or a transceiver.

In embodiments, the network communication device 4010 may comprise a voice receiver and transmitter disposed in the container cap portable housing for receiving and/or sending voice signals over a communications network. In embodiments, the network communication device 4010 may be configured to receive data for the electrical circuit and/or to transmit signals from the electrical circuit.

In embodiments, the electrical circuit 4010 may comprise logic for generating data for transmission when the cap housing is removed from the open end of the container, and to transmit that data over the communications network.

In embodiments, the electrical circuit 3800 may further comprise an electronic display screen 4030. In embodiments, the electrical circuit 3800 may further comprise an electronic memory 4032, and the electrical circuit 3800 may be configured to record in the electronic memory 4032 data, e.g., a time and date, and number of times removed, when the cap housing is removed from the open end of the container, and to display that data on the display 4030.

In embodiments, the electrical circuit may be configured with a current limiter 4024 to limit a level of the electrical current supplied to the shape memory material component 3816 to a predetermined electrical current range. In embodiments, this feature may be implemented via a comparator for comparing the supplied electrical current to a threshold, and generating a limit signal when the threshold is reached.

In embodiments, the electrical circuit may be configured with a network communication device 4310 disposed in the cap housing. In embodiments, the electrical circuit may be configured with a tracking element 4310 comprising one or more selected from the group of a GPS circuit and a cellular telephone circuit for location determination. In embodiments, the electrical circuit may be configured to transmit location data obtained from the tracking element 4310 over a communications network via the network communication device.

Note that electronic diagrams of FIG. 38-40 may be used to implement all of the embodiments described herein. Note that in embodiments, only selected ones of the elements shown in FIG. 40 may be used. In embodiments, all of the elements shown in FIG. 40 may be used.

In embodiments as shown in FIGS. 10, 17 and 18, the cap housing may comprise a key pad 1080, 1700, or 1800 with buttons or touch elements for controlling the electrical circuit to supply electrical current from the electrical current source to the shape memory material component 1050 to cause the shape memory material component to change between the first length and/or shape and the second length and/or shape. In embodiments, the keypad may be comprised of thin-film and may comprise a printable circuit with graphine-based ink. The keypad 1080 may be disposed on a surface of a container cap 1000 or on the container 1010. In embodiments, the keypad may be remote from the container cap and container, and comprise a transmitter for sending control signals to a receiver or other network device 4010 in the electrical circuit in the container cap to thereby open the container cap.

FIGS. 19-24 illustrate embodiments of a container cap consistent with the invention. In the embodiments of FIG. 19-24, a container cap 1900 may comprise a plurality of portions that may be separable in whole or in part. In embodiments, the container cap 1900 may comprise a first portion 2100 and a second portion 2110. In embodiments, the first and second portions may comprise opposing parallel surfaces 2140, 2142. The first portion 2100 may comprise an element or projection 2160 that projects from the surface 2140 thereof. In embodiments, the element 2160 may be shaped to include a side extension 2162 that extends approximately in the direction of the parallel surface 2140. In embodiments, this side extension 2162 may extend from a side surface of the projection 2160 at or near an end thereof.

In embodiments, the second portion 2110 may comprise a recess 2035 in which the projection 2160 fits when the portions 2100 and 2110 are fitted together. In embodiments, the recess 2035 may further include an interference block 2050 with a side projection 2052. In embodiments, the interference block 2050 may be laterally slidable within the recess 2035 in a direction that is parallel to the face or plane surface 2142 on the second portion 2110, so that the side projection 2052 fits in registration with the side extension 2162 within the recess 2035 when the interference block 2050 is in a first interfering position, and is out of registration when the interference block is in a second non-interfering position. Note that the term “parallel” encompasses slide angles that are within a range of 1-10 degrees of parallel.

In embodiments, a shape memory material component 2045 may be attached directly or indirectly to the interference block 2050 and may be anchored at one end thereof to an internal wall of the recess 2035. When the shape memory block has a first length and/or shape, the interference block 2050 is in the first interfering position so that the side projection 2052 and the side extension 2162 fit in registration and prevent the first portion 2100 from being pulled away or separated from the second portion 2110. In embodiments, this first interfering position may be the normal position for the interference block 2050 when the shape memory material component is not energized. When the shape memory material component is energized to take a second length and/or shape, the interference block 2050 slides to the second non-interfering position with the side projections 2052 and 2062 out of registration, allowing the first portion 2100 and the second portion 2110 to be pulled apart as shown in FIG. 21. In other embodiments, the normal position for the interference block 2050 when the shape memory material component is not energized may be the non-interfering second position. In embodiments, the shape memory material component may take the configuration of a wire.

In embodiments, the shape memory material component 2045 may comprise a rectangular block. In embodiments, the shape memory material component 2045 may comprise a band. In embodiments, the shape memory material component 2045 may comprise a tubular element. The invention is not intended to be limited by the shape that the shape-memory material component can take.

In embodiments, the interference block 2050 may be biased into an interfering position or a non-interfering position. In the embodiments shown in FIGS. 20 and 23, the interference block 2050 is biased into an interfering position by a spring 2037. Note that a variety of other biasing elements may be used in place of the spring.

In embodiments, the shape memory material component may be replaced by a micro-motor configured to slide the interference block 1170 between the first interfering position and the second non-interfering position in accordance with control signals provided to the micro-motor. In embodiments, current may be supplied to the micro-motor under control of the electrical circuit and the switching device to move the interference block between an interfering position and a non-interfering position.

FIG. 22 is a top view of the embodiments of FIGS. 19-22 providing a view of the recess 2035 without the interference block 2160 therein. FIGS. 23-24 illustrate side cross-section views of the embodiments of FIGS. 19-22.

Figure 25:
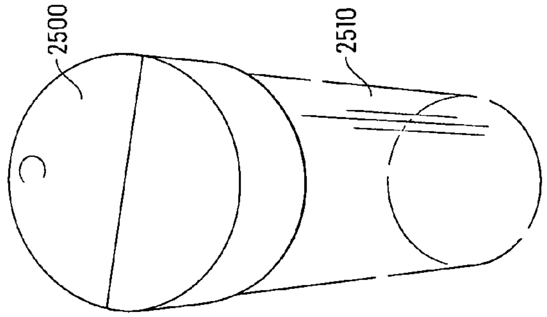
FIG. 25 is a perspective view of an embodiment of a container and container cap.

FIGS. 25-29 illustrate further embodiments of a container cap consistent with the invention. FIG. 25 illustrates a container cap 2500 that fits on a container 2510. In the embodiments the container cap 2500 may comprise a plurality of portions that may be separable in whole or in part. In embodiments, the container cap 2500 may comprise a first portion 2600 and a second portion 2610 with opposing surfaces. In embodiments, the first portion 2600 may comprise two pieces 2620 and 2622 on the same plane positioned to be rotatable or slidable on a track 2615 within the first portion 2600. In embodiments, each of the two pieces may comprises a fractional portion of a disk that is positioned to slide along the track or rotate around the track in the first portion.

In embodiments, the second portion 2610 may comprise a track on the same plane as the track in the first portion 2600 and positioned to receive at least a portion of the two pieces therein when the pieces or fractional disks 2620 and 2622 are rotated away from each other. In embodiments, the second portion 2610 may have a recess 2650 (illustrated in dashed lines in FIG. 26B and FIG. 27) defined therein to receive the pieces or rotated fractional disks 2620 and 2622 therein.

Figure 28:
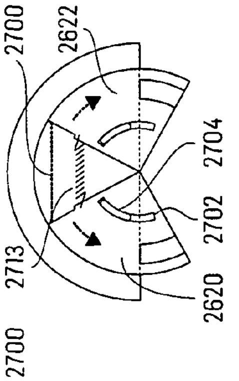
FIG. 28 is a top view of the container cap embodiment of FIG. 26 with the fractional disks rotated into the second portion.

In embodiments, the pieces or fractional disks 2620 and 2622 may ride in close adjacency to an inner circular wall of the first and second portions 2600 and 2610. In embodiments, the tracks 2615 may be in the shape of a semi-circle within the first portion 2600 and the second portion 2610. FIG. 26B illustrates that the pieces or fractional disks 2620 and 2622 may be rotated outward or away from each other to move outside the periphery of the first portion 2600, and on to the comparable track on the same plane into the recess 2650 within the second portion 2610. This rotated position is shown in FIG. 28, which illustrates only the first portion 2600.

In embodiments, a spring 2713 or other device may be provided to bias or load the fractional disks in the interfering position.

Figure 27:
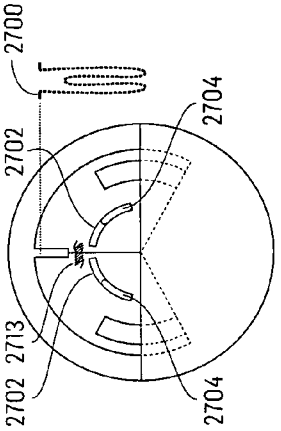
FIG. 27 is a top view of the container cap embodiment of FIG. 26 with the fractional disks not rotated into the second portion.
Figure 29A:
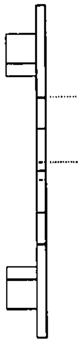
FIG. 29A is a side view of the first portion for the embodiment of FIG. 26.
Figure 29B:
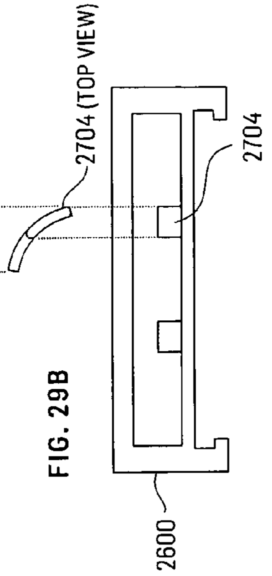
FIG. 29B is a side view of the first portion for the embodiment of FIG. 26 with the fractional disks removed.

In embodiments, a shape memory material component 2700 is illustrated connected at one end thereof to the piece or fractional disk 2620, and connected at the other end thereof to the piece or fractional disk 2622. When the shape memory material component 2700 has a second length and/or shape, the pieces or fractional disks 2620 and 2622 are held close together in a non-interfering position, as illustrated in FIG. 27. When the shape memory material component 2700 has a first length and/or shape as illustrated in FIG. 28, the pieces or fractional disks 2620 and 2622 are held apart, causing the pieces or fractional disks 2600 and 2610 to move or to rotate at least partially into the track of the second portion 2610, in the interfering position. In embodiments, the shape memory material component 2700 may be in the form of a wire. However, as noted previously, the shape memory material component 2700 may take any configuration. The particular configuration thereof is not limiting on the invention. In embodiments, the shape and/or length of the shape memory material component 2700 shown in FIG. 27 may comprise the shape and length when energized with an electrical current, and the shape and length of the shape memory material component 2700 shown in FIG. 28 may comprise the shape and/or length when not energized with an electrical current.

In embodiments, a slot 2702 (see FIG. 27) may be formed in each of the disks 2620 and 2622, and an projection 2704 may rise from the floor 2915 of the first portion 2600 or descend from the ceiling of the first portion to fit and ride within the slot 2702. See FIGS. 26-28, and FIG. 29 (which is a side view of the first portion with the rotatable disks removed) for a view of the slot. In embodiments, a purpose of the slots 2702 and projections 2704 is to prevent the disks 2620 and 2622 from being pulled apart when the pieces or fractional disks 2620 and 2622 are rotated into the interfering position. Accordingly, the projections 2704 may be high enough to prevent the fractional disks 2620 and 2622 from being lifted out of the slots 2702.

In embodiments, arced projections 2624 may project upward from the top surface of the pieces or fractional disks 2620 and 2622, and/or may project downward from a bottom surface. In embodiments, the recess 2650 in the second portion 2610 may comprise curved recess portions therein opposite the arced projections. When the arced projections 2624 are rotated into the opposite curved recess portions, the arced projections fit in registration with the curved recess portions of the recess 2650 to prevent the pieces or fractional disks 2620 and 2622 from being pulled apart, e.g., lateral movement of the portions 2600 and 2610 is prevented.

Referring to FIGS. 30-37, further embodiments of the container cap are disclosed. A container cap is illustrated that may comprise a top portion 3000 and a bottom portion 3100. In embodiments, the top portion 3000 may be hinged at one end thereof to the bottom portion 3100. The hinge may be seen in the views of FIGS. 34-37. In embodiments, the bottom portion may fit over a bottle container 3260. A lip 3200 of the bottle container 3260 is illustrated in exploded view in FIG. 32.

In other embodiments, the bottom portion 3100 may be integral with the container 3260.

In embodiments, instead of a hinge connection, the top and bottom portions may be threaded, so that the top portion may be screwed onto the top portion.

The container cap 3000 may comprise a recess 3040 disposed to extend from inside the container cap to an opening in a side of the container cap. An interference block 3010 may be disposed within the recess 3040, and slidable within the recess 3040 to project through the opening into a recess 3130 set in a side of the container 3100, to thereby be in an interfering position. The recess 3040 may be configured in the container cap 3000 to allow the interference block 3010 to be pulled or slid into a non-interfering position with the interference block not extending into the recess 3130 in the container. Thus, in embodiments, the interference block 3010 may be moveable between the interfering position (shown in FIGS. 31, 34 and 36) and the non-interfering position (shown in FIGS. 35 and 37) with the interference block 3010 pulled into the recess 3040 so that the end of the interference block is clear of the recess 3130.

In embodiments, the recess 3130 and the end of the interference block 3010 that fits into the recess 3130 may be beveled or otherwise shaped to allow the interference block to be forced back to the non-interfering position to close the container cap 3000 on the container 3100. In embodiments where the top portion 3000 is screwed or twisted onto the bottom portion 3100, the end of the interference block 3010 that fits into the recess 3130 may be beveled on one or more of the sides thereof to so that the interference block can slip into the recess even when it is not in exact registration with the recess 3130. In embodiments, the interference block 3010 may be biased into its interfering position per FIG. 31. By way of example, the biasing may be accomplished by a spring 3014 connected at one end thereof to an internal wall of the recess 3040 of the container cap 3000, and connected at the other end thereof to the interference block 3010.

In embodiments, a shape memory material component 3012 is illustrated connected at one end thereof to an internal wall of the recess 3040 of the container cap 3000, and connected at the other end thereof to the interference block 3010. When the shape memory material component 3012 has a first length and/or shape, an end of the interference block is extended into the recess 3130, as illustrated in FIGS. 31 and 36. When the shape memory material component 3012 has a second length and/or shape, the interference block 3010 is pulled into the recess 3040 of the container cap, as illustrated in FIGS. 35 and 37, so that the container cap 3000 can be swung or tilted up on the hinge 3120 to allow access to the contents of the container 3100. In embodiments, the shape memory material component 3012 may be in the form of a wire. However, as noted previously, the shape memory material component 3012 may take a variety of different configurations. The particular configuration thereof is not limiting on the invention. In embodiments, the shape and length of the shape memory material component 3012 shown in FIGS. 35 and 37 may comprise the shape and/or length when energized with an electrical current. The shape and/or length of the shape memory material component 3012 shown in FIGS. 31, 34 and 36 may comprise the shape and/or length when not energized with an electrical current.

In embodiments, it may be necessary to apply an electrical current to briefly cause the shape memory material component to take its non-interfering length and/or shape in order to close the container cap on the container. In embodiments, this application of electrical current may be applied by inserting a code in the keypad. In embodiments, there may be a button disposed on a surface of the container cap, which button is only active for controlling energization when the container cap has been removed from the container, to cause application of electrical current in order to close the container cap on the container.

In embodiments, it may not be necessary to apply an electrical current to close the container cap on the container. In such embodiments, a beveling or other design configuration may be used for the interference block so that the container cap may be closed on the container with the application of a certain minimum force.

Figure 41:
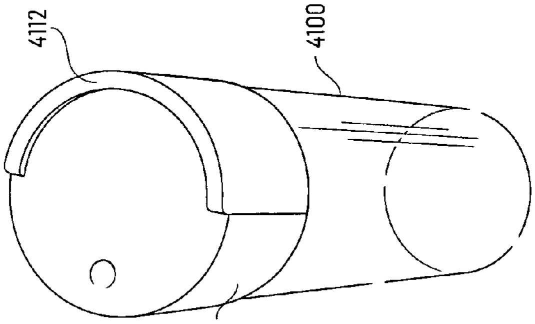
FIG. 41 is a perspective view of a further embodiment of the container cap.
Figure 42:
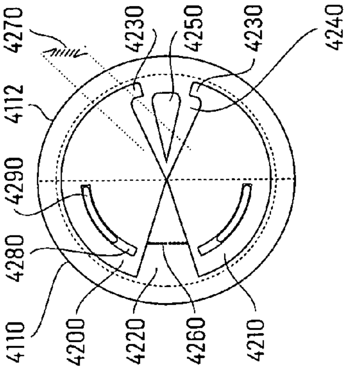
FIG. 42 is a top view of the embodiment of FIG. 41 with the container cap unlocked.
Figure 43:
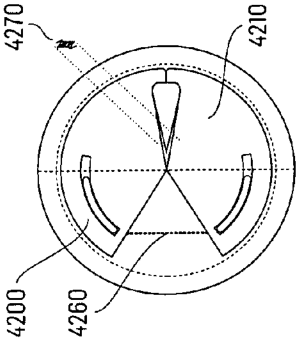
FIG. 43 is a top view of the embodiment of FIG. 41 with the container cap locked.
Figure 44:
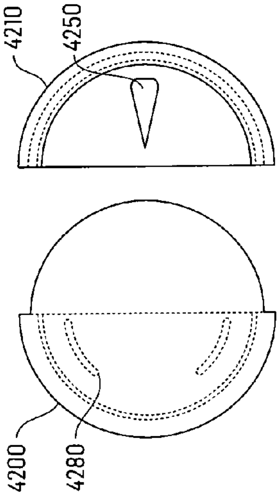
FIG. 44 is an exploded top view of the embodiment of FIG. 41 with the container cap without the elements 4200 and 4210.
Figure 45:
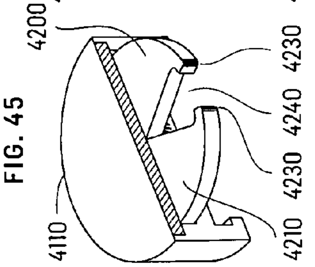
FIG. 45 is a perspective view of the portion 4110 in unlocked position.
Figure 46:
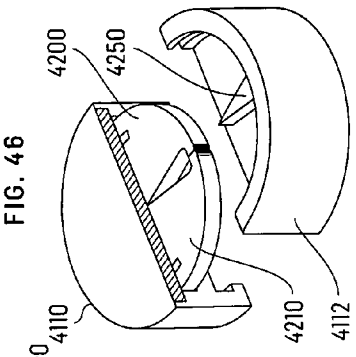
FIG. 46 is an exploded perspective view of the portions 4110 and 4112 in a locked position.
Figure 47:
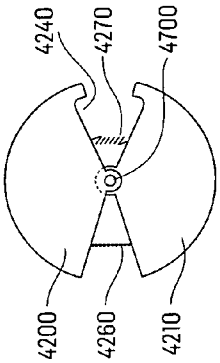
FIG. 47 is a top view illustrating only the moveable sections 4200 and 4210.

Referring to FIGS. 41-47, a further embodiment of the container cap is illustrated. FIG. 41 illustrates a container 4100 with a multi-piece cap thereon. In embodiments, the multi-piece cap may comprise a first portion 4110 and a second portion 4112.

FIGS. 42-47 illustrates that in embodiments, the first portion 4110 may comprise multiple moveable pieces. In the embodiments of FIGS. 42-47, two moveable pieces 4200 and 4210 are show. In the embodiments shown, the two moveable pieces 4200 and 4210 may comprise fractions of disks that are slidable/rotatable around a track on the perimeter of the first portion 4110. In embodiments, the two fractional disks may be shaped so that there is a first opening 4220 therebetween at one end of the disks within the first portion 4110, and there is a second opening 4240 therebetween at the other end of the disks, where the disks extend into the second portion 4112. At the other end of the fractional disks that extends into the second portion 4112, each of the fractional disks comprises a projection 4230 that projects in the circumferential direction so that the respective projections 4230 project toward each other as shown in FIGS. 42, 43, 44, 45, 46, and 47. Thus, the projections 4230 are positioned to oppose each other and to form a boundary of the second opening 4240 defined by the fractional disks adjacent the other end.

The second portion 4112 comprises an upward or downward projection 4250 configured to fit within the second opening 4240 made by the fractional disks 4200 and 4210.

In embodiments, the fractional disks 4200 and 4210 may be biased into a rotated position where the circumferential projections 4230 on the respective disks are close to each other and in some embodiments, may be touching, to lock the projection 4250 within the opening 4240. In embodiments, this biasing into a locked position may be implemented via a spring 4270 disposed between the fractional disks 4200 and 4210 within or adjacent the second opening 4240. In embodiments, the spring may be connected to each of the fractional disks 4200 and 4210 on sides thereof defining the second opening 4240.

In embodiments, a shape memory material component 4260 may be positioned with respect to the fractional disks 4200 and 4210 to rotate or otherwise move the fractional disks so that the circumferential projections 4230 separate or move away from each other to no longer trap the projection 4250, and thereby allow the second portion 4112 to be separated from the first portion 4110. In embodiments, the shape memory material component 4260 may comprise a wire connected to each of the fractional disks 4200 and 4210 on sides thereof defining the first opening 4220. In embodiments, the shape memory material component 4260 may take a variety of different configurations and positions relative to the fractional disks 4200 and 4210 to cause movement of the disks to unlock the container cap when the shape memory material component 4260 is energized. As noted previously for other embodiments, the shape memory material component 4260 may be in a rectangular configuration or any other convenient configuration to cause movement of the fractional disks when the shape memory material component 4260 is energized.

In other embodiments, the biasing of the fractional disks 4200 and 4210 may be to an unlocked position where the projections 4230 are separated so that the projection 4250 on the second portion 4112 is not trapped. In this configuration, the shape memory material component 4260 may be positioned and configured to move the fractional disks 4200 and 4210 to a locked position wherein the projections 4230 move towards each other to trap the projection 4250 to prevent the second portion 4112 from being separated from the first portion 4110.

In embodiments, structure may be included to prevent the fractional disks from being removed from the first portion 4110. In embodiments, this structure may comprise a circumferential slot 4280 formed in each of the fractional disks 4200 and 4210. The structure may further comprise a projection 4290 projecting upward from a floor surface of the first portions 4110 or downward from a ceiling portion of the first portion to fit within the slot 4280. In this embodiment, the rotation of the fractional disks is limited by the circumferential length of the circumferential slots 4280, as can be seen from FIGS. 42 and 43.

In embodiments, the fractional disks 4200 and 4210 may rotate on an axis pin 4700. In embodiments, the biasing of the fractional disks 4200 and 4210 into a closed or locked position may be accomplished by spring-loading the axis pin 4700.

Referring to FIGS. 48-59, a further embodiment of the container cap is illustrated. In the embodiments of FIGS. 48-52, a cap housing is shown comprising a first portion 4800 and a second portion 4820. In embodiments, the second portion 4820 is configured to be pulled up to a lip 4850 (shown in exploded view in FIG. 49) of an open container 4860. In embodiments, the first portion 4800 may be hinged to the second portion at one end thereof. In embodiments, the hinge (not shown) may fit in a recess 4824. In other embodiments, the first portion and the second portion may be threaded so that the first portion may be twisted onto the second portion.

In embodiments, an interference block 4806 may comprise a first clip piece 4806 with an end 4808 thereof biased toward an end 4810 of a second clip piece 4807 to form a clip 4804. In embodiments, the clip 4804 may be disposed within a recess 4802 in the first portion 4800. In embodiments, the second clip piece 4807 may comprise a wall of the recess in the first portion 4800.

In embodiments shown in FIGS. 48-52, the clip 4804 may be positioned perpendicular and projecting toward the opening of the container, with the outer periphery of the opening defined by the lip 4850.

In embodiments, the second portion 4820 may comprise a knob 4822 extending from a surface of the second portion 4820, with the knob having one or more indents 4824 formed below a top portion of the knob, and with the knob positioned in alignment with the clip 4804 so that clip fits around the knob and into the one or more indents 4824 when in a locked position, to thereby prevent the first portion 4800 from being separated from the second portion 4820.

In embodiments shown in FIGS. 53-59, the clip 4804 may be positioned in parallel with the opening of the container. In embodiments illustrated in FIGS. 58-59, the knob 4822 may comprise a head portion 4824 and an indented portion 4826. In embodiments, the indented portion 4826 may be in a shape of a triangular base that has one corner or edge 4828 thereof pointing toward the clip 4804.

In embodiments, a shape memory material component 4870 may be connected between the first clip piece 4806 and the second clip piece 4807 so that when the shape memory material component 4870 has the first length and/or shape, the interference block 4806 is disposed around the knob 4822 in the indents to prevent separation of the first portion from the second portion, and when the shape memory material component has the second length and/or shape, the interference block allows the knob to be separated from the clip 4804 to allow separation of the first portion from the second portion.

In embodiments, the first clip piece 4806 may be hinged to the second clip piece 4807 of the first portion by a hinge 4812. In embodiments, biasing of the end 4808 of the first clip piece 4806 toward the end 4810 of the second clip piece 4807 may be accomplished by spring-loading the hinge 4812. In embodiments, the biasing of the clip piece toward the end 4810 of the wall of the first portion may be accomplished be connecting a spring between the clip piece 4806 and the end 4810 of the wall of the first portion.

FIGS. 60-64 illustrate further embodiments of the invention. The cap housing may comprise a first portion 6000 and a second portion 6020 with respective opposing parallel surfaces 6008 and 6028. In embodiments, an interference block may comprise a clip 6100 comprising a first clip piece 6110 with an end thereof biased toward an end of a second clip piece 6120. In embodiments, the clip 6100 may be positioned within a recess 6005 formed in the parallel surface 6008 of the first portion 6000, but extending partially from the surface of the parallel surface 6008 of the first portion.

In embodiments, the second portion 6020 may comprise a projection 6022 extending from within a recess 6024 formed in the parallel surface 6028 of the second portion 6020.

In embodiments, the clip 6100 may be positioned so that the end of the first clip piece and the end of the second clip piece extend into the recess on either side of the projection 6022 to fit around and behind the projection 6022 in the second portion 6020 when in a locked position, to thereby prevent the first portion 6000 from being separated from the second portion 6020.

In embodiments, a shape memory material component 6350 may be connected between the first clip piece 6110 and the second piece 6120 so that when the shape memory material component has the first length and/or shape, the ends of the first and second clip pieces extend around and behind the projection 6022 in the second portion 6020 to prevent separation of the first portion from the second portion, and when the shape memory material component 6350 has the second length and/or shape, the ends of the first and second clip pieces are moved apart to allow separation of the first portion 6000 from the second portion 6020.

In embodiments, biasing of the first clip piece 6110 toward the second clip piece 6120 may be accomplished by spring-loading a pin 6300 connecting the clip pieces. In embodiments, the biasing may be accomplished in another way using springs or other structure.

FIGS. 65-85 illustrate further embodiments of the invention. In the figures, a rectangular pill dispenser is illustrated. However, the pill dispenser may take a variety of other shapes.

In embodiments illustrated in FIGS. 65-85, a cap housing 6500 comprises one or more hinges 6512 at a first side 6510 thereof to hinge the cap housing to a first side of the open end of a container 6700.

In embodiments, multiple hinges 6512 may be used. Note that for all embodiments with hinges, the hinge design may take a variety of different configurations and is not limiting on the invention.

In embodiments, an interference block 7100 (shown in FIGS. 71-72) may be positioned at a second side 7108 of the cap housing 6500 opposite to the side with the hinge.

In embodiments, the interference block 7100 may comprise a clip with a first clip piece 7202 and a second clip piece 7204. In embodiments, the second clip piece 7204 may be integral with a side wall of the cap 6500. See FIGS. 71-72. In embodiments, the clip 7100 may be biased so that the ends of the clip pieces are biased toward each other for a closed or locked position. In embodiments, the biasing may be via spring-loading of a pin 7206 connecting the first and second clip pieces. Other methods of biasing may be used and the invention is not limited to a particular method of biasing.

In embodiments, a second side 7150 of the open end of the container opposite to the first end may comprise a knob 7160 extending from a surface 7152 of the second side 7150 of the open end of the container. In embodiments, the knob may have at least one indent 7162 formed below a top portion of the knob 7160. In embodiments, the knob 7160 may be positioned in alignment with the clip 7100 so that ends of the clip fits around the knob 7160 into the indent 7162 when in a locked position to thereby prevent the cap housing from being separated from the open end of the container.

In embodiments, a shape memory material component 7240 may be connected between the clip pieces 7202 and 7204 of the clip 7100 so that when the shape memory material component 7240 has the first length and/or shape, the interference block is disposed to around the knob in the at least one indent to prevent separation of the cap housing from the open end of the container, and when the shape memory material component has the second length and/or shape, so that the clip pieces 7202 and 7204 are separated to allow the separation of the cap housing from the open end of the container.

Figure 73:
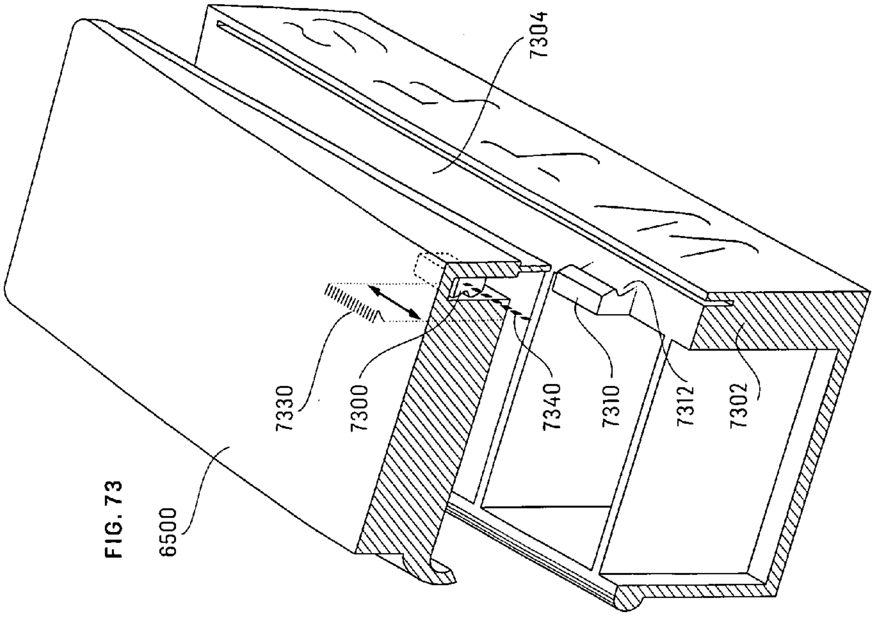
FIG. 73 is a perspective exploded view of further embodiments of a lid and a container consistent with the invention.
Figure 74:
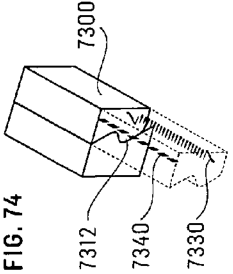
FIG. 74 is a perspective exploded view of further embodiments of a locking mechanism that may be used with embodiments of the invention.
Figure 71:
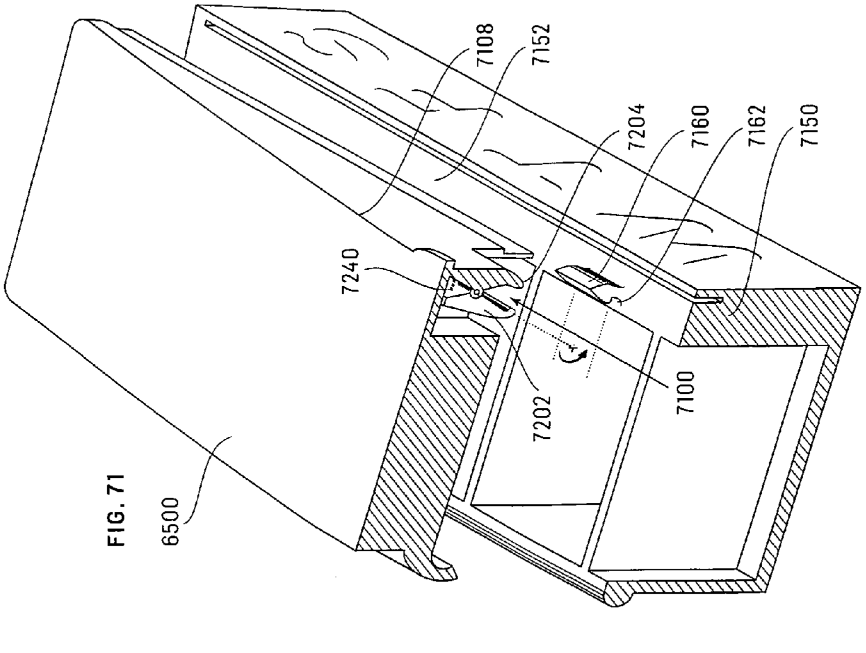
FIG. 71 is a perspective exploded view of further embodiments of a lid and a container consistent with the invention.
Figure 72:
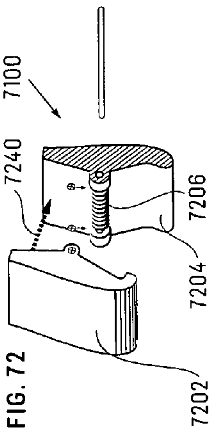
FIG. 72 is a perspective exploded view of further embodiments of a locking mechanism that may be used with embodiments of the invention.

FIGS. 73-74 illustrate embodiments where the interference block comprises a slidable block 7300 that slidable between a first locking position shown in FIG. 74, and a second unlocked position shown in phantom lines in FIG. 73.

In embodiments, a second side 7302 of the open end of the container opposite to the first end comprises a knob 7310 extending from a surface 7304 of the second side of the open end of the container, with the knob 7310 having at least one indent 7312 formed below a top portion of the knob. In embodiments, the knob 7310 may be positioned so that the interference block 7300 may be slid so that a portion thereof fits in registration (see FIG. 74) with the indent 7312 in the knob 7310 when in a locked position to prevent the container cap from being separated from the second side of the container.

In embodiments, a shape memory material component 7340 may be connected to one end of the interference block 7300 so that when the shape memory material component 7340 has the first length and/or shape as shown in FIG. 74, the interference block is positioned to fit in registration with the indent 7312 in the knob for the locked position to prevent separation of the cap housing from the open end of the container. When the shape memory material component 7340 has the second length and/or shape, the interference block is slid so that it is no longer in registration with the indent 7312 in the knob thereby allowing separation of the cap housing from the open end of the container.

In embodiments, the slidable interference block 7300 may be biased into the locked position in registration with the indent 7312 in the knob 7310. In embodiments, this biasing may be accomplished via a spring 7330. However, as noted for other embodiments, the method of biasing is not limiting on the invention.

Figure 77:
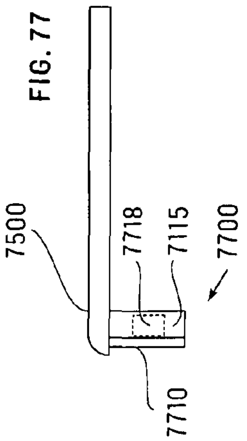
FIG. 77 is a side view of the lid 7500 of FIG. 75 for a container embodiment of the invention.
Figure 78:
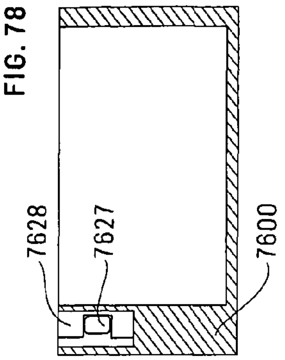
FIG. 78 is a side cross-section view of the bottom portion of FIG. 76 for a container embodiment of the invention.
Figure 75:
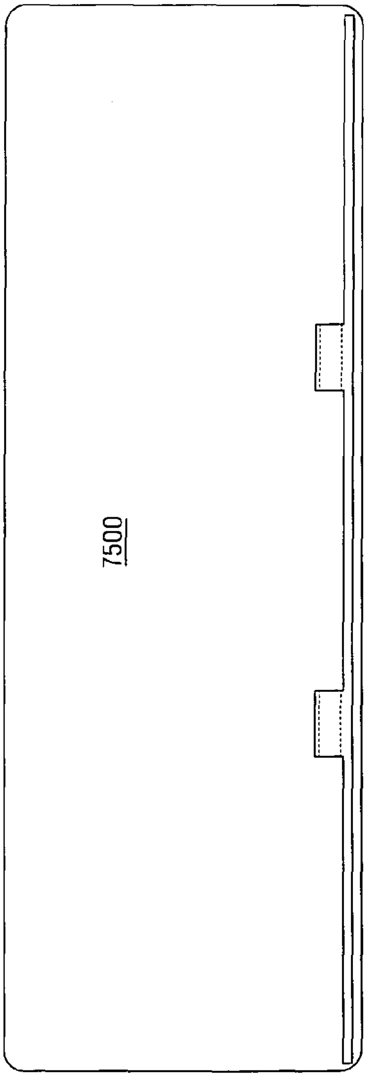
FIG. 75 is a top view of a lid 7500 for a container embodiment of the invention.
Figure 76:
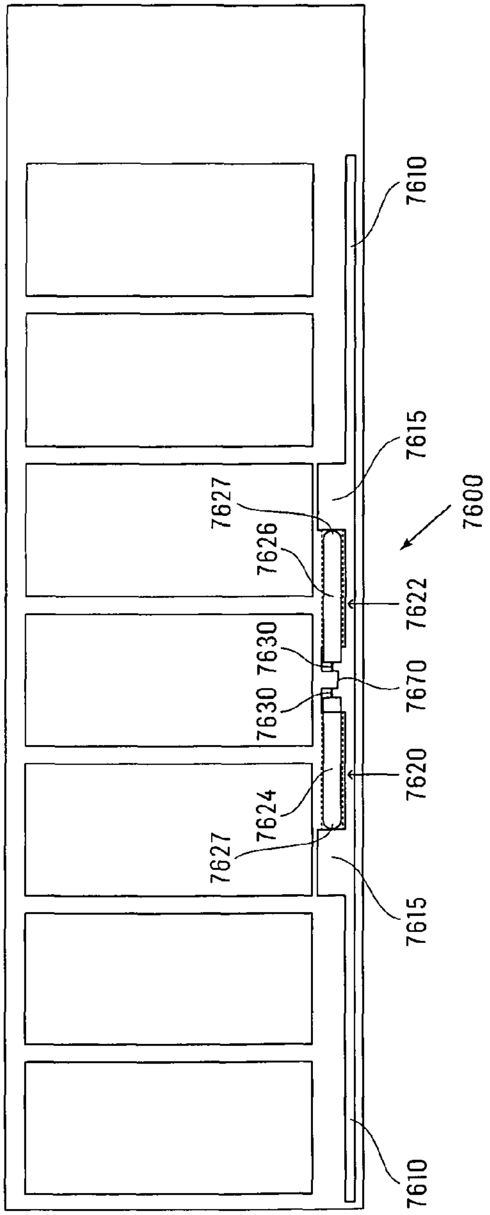
FIG. 76 is a top view of a bottom portion of 7600 for a container embodiment of the invention.
Figure 79:
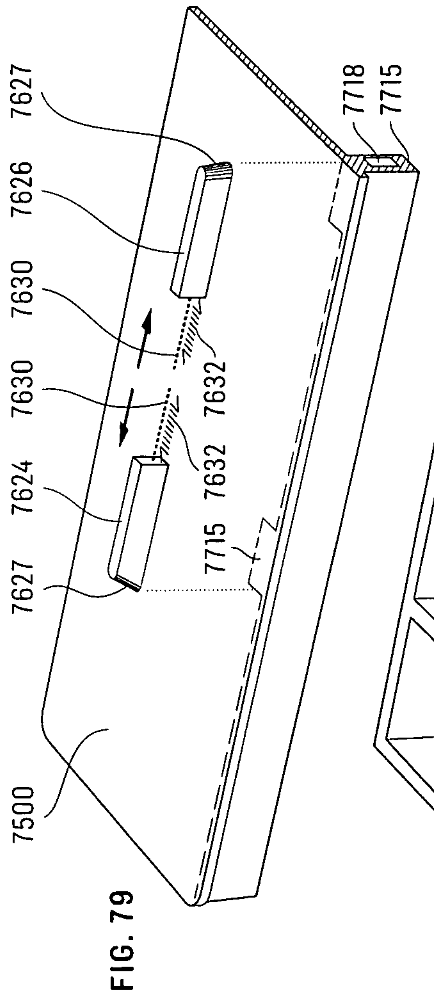
FIG. 79 is a perspective view of the lid 7500 of FIG. 75 for a container embodiment of the invention, illustrating exploded interference blocks in a locking position.
Figure 80:
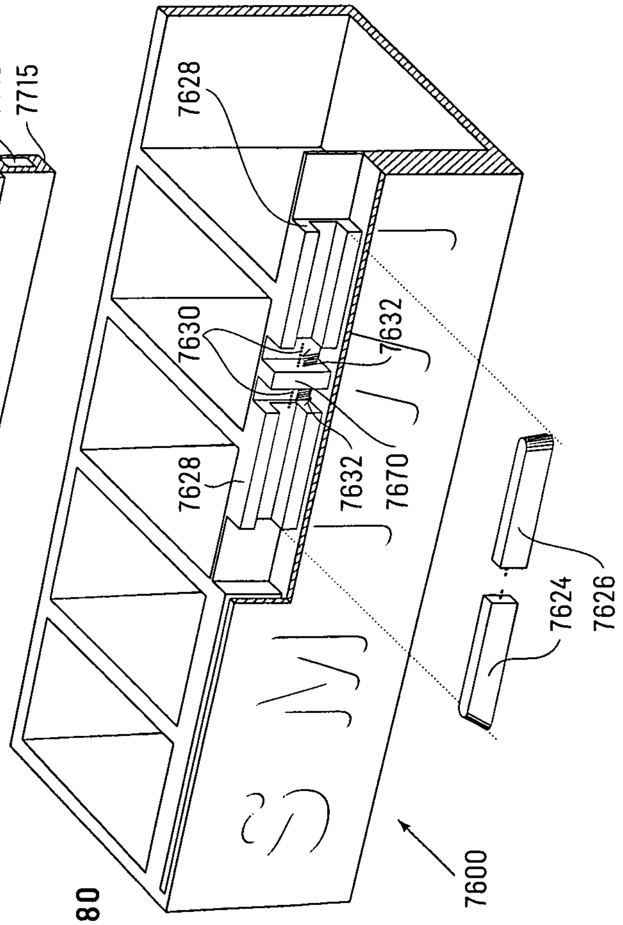
FIG. 80 is a perspective cut-away view of the bottom portion of FIG. 76 for a container embodiment of the invention illustrating the tracks with the interference blocks removed.

Referring to FIGS. 75-80, a further embodiment of the invention is illustrated. FIG. 75 illustrates a lid 7500 for a container. FIG. 76 illustrates a container portion 7600 for holding pills or other items. In embodiments, two narrow slot recesses 7610 may be formed in a top surface of the container portion 7600 on one side thereof for receiving portions of a downwardly extending lip 7700, that is shown in FIG. 77.

In embodiments, the slot recess 7610 may further comprise two enlarged recesses 7615 on either side of a lock mechanism 7620 and 7622. In embodiment, the lock mechanism may be disposed in the wall of the container portion 7600 and may comprise laterally sliding interference blocks 7624 and 7626.

In embodiments, the downwardly extending lip 7700 (shown in FIG. 77) may comprise a first portion 7710 of the lip shaped to be received in the narrow slot recesses 7610. The downward extending lip 7700 may further comprise two enlarged portions 7715 shaped to fit in the enlarged recesses 7615. In embodiments, the enlarged portions 7715 may each comprise a recess 7718 for receiving an end 7627 of the sliding interference blocks 7624 and 7626. In embodiments, the interference blocks 7624 and 7626 may be biased into a locked position within the respective recesses 7718. In embodiments, this biasing may be accomplished via a spring 7632 (see FIGS. 79 and 80) connected between a base portion 7670 of the container portion (see FIG. 80) and one end of the respective sliding interference blocks 7624 and 7626. In embodiments, other structure for accomplishing the biasing may be used, as noted previously.

In embodiments, a shape memory material component 7630 may be connected between the base portion 7670 of the container portion (see FIG. 80) and the one end of the respective sliding interference blocks 7624 and 7626. In embodiments, when the shape memory material component 7630 has the first length and/or shape, the ends 7627 of the interference blocks 7624 and 7626 are positioned within the respective recesses 7718 in the enlarged portions 7715 of the downwardly extending lip 7700 of the lid to prevent separation of the lid 7500 from the open end of the container 7600. When the shape memory material component 7630 is energized to have the second length and/or shape, the ends 7627 of the interference blocks are retracted from the respective recesses 7718 to allows separation of the lid from the open end of the container 7600.

As noted previously, the shape and positioning of the shape memory material component are not limiting on the invention, and may take a variety of other convenient shapes and positions within the embodiments. Likewise, the number of sliding interference blocks in the lock and the number of enlarged portions in the lid and their positioning may vary and are not limiting on the invention.

Note that various configurations of controls for opening the container lid and displays are shown in FIGS. 65, 66, 67, 69, 70, 81, 82, 83, and 85. The controls may comprise buttons 6600 and 7700 disposed on the lid of the container, per FIGS. 65, 66, 70, 82, or buttons 6750 disposed on a portion of the container base 6700, per FIGS. 67, 69, 81, 83, and 85. The placement of the buttons or other control elements may take a variety of configurations and is not limiting on the invention.

Figure 82:
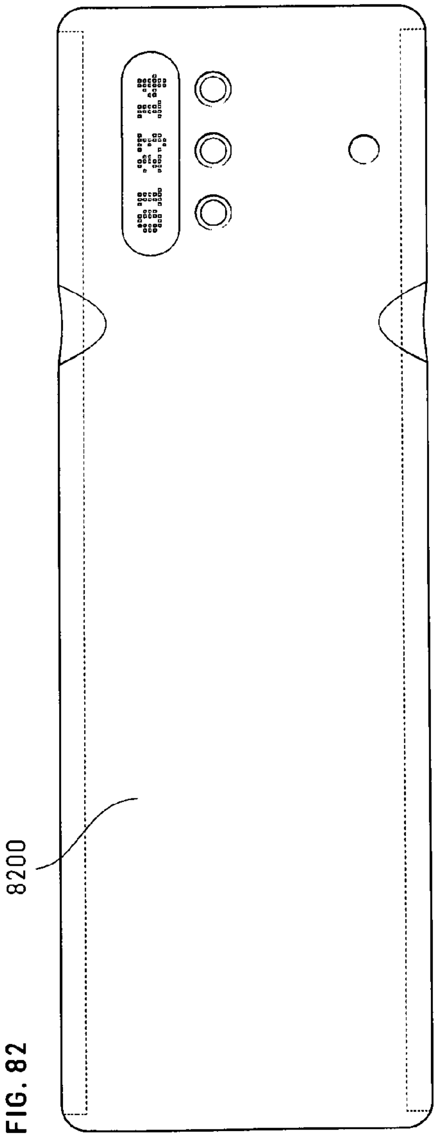
FIG. 82 is a top view of embodiments of the container with a slidable lid and a different button design.

Referring to FIGS. 81-85, embodiments of a container 8100 with a slidable transparent lid 8105 are illustrated. In embodiments, the container may be separated into a plurality of compartments 8110. An embodiment of control elements such as button 6750 is illustrated on a surface of the container 8100. In embodiments, a display 8230 may be positioned on the container 8100, as shown in the figure. FIG. 82 illustrates a different configuration of the control elements and the display on or within the lid 8200. Note that in this configuration, the electronics for the locking mechanism and for the communication components may be positioned in the lid.

Figure 83:
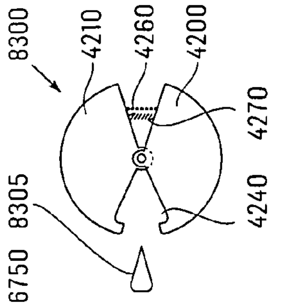
FIG. 83 is a top view of embodiments of a lock that may be used with the container of FIG. 81.
Figure 81:
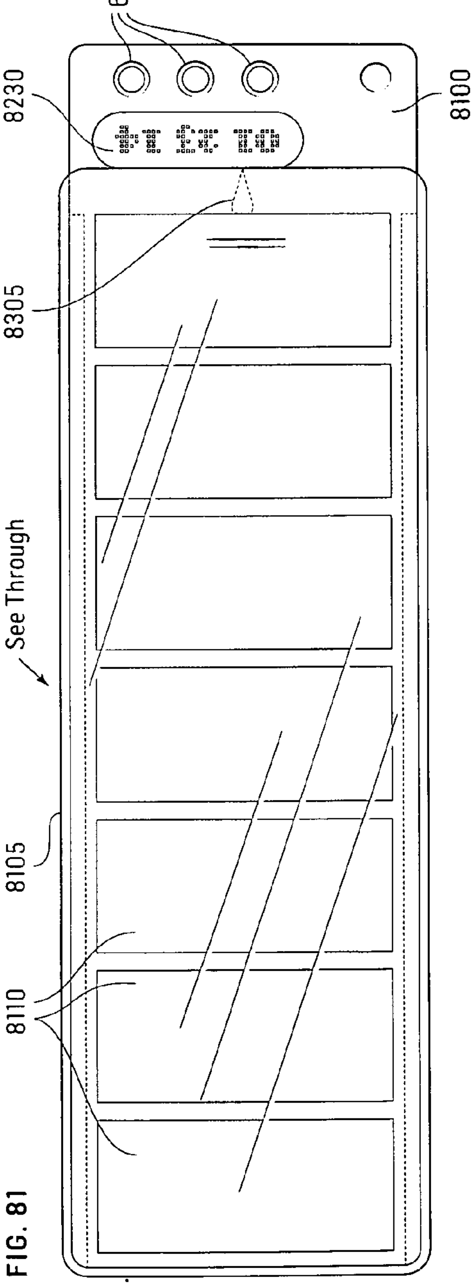
FIG. 81 is a top view of embodiments of the container with a transparent slidable lid.
Figure 84:
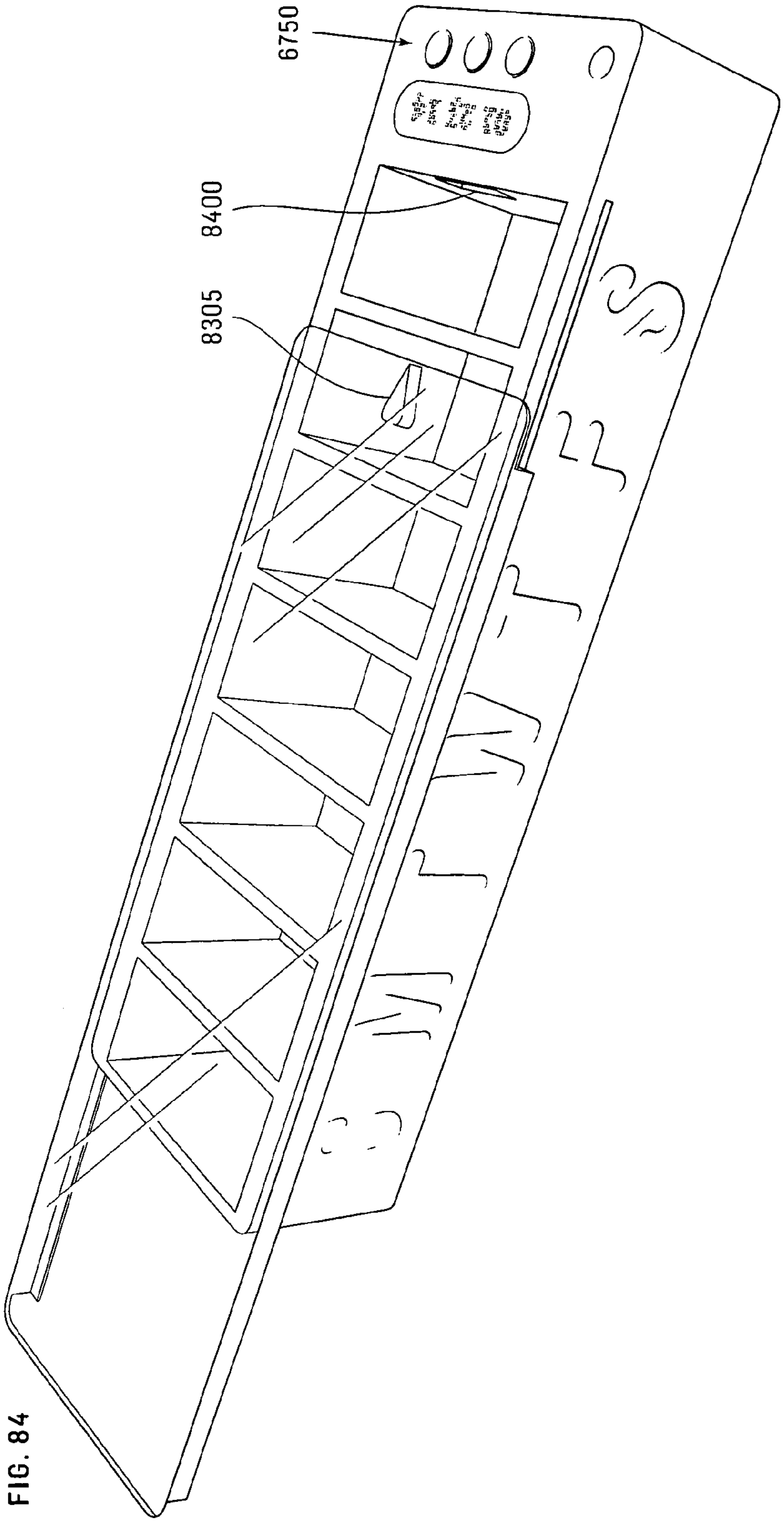
FIG. 84 is a perspective view of embodiments of the container
Figure 85:
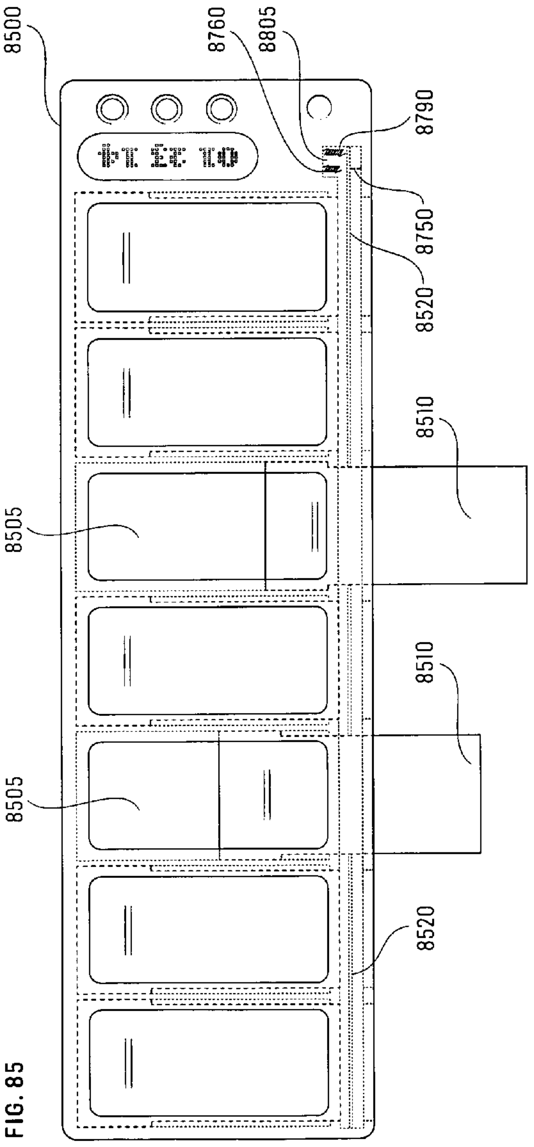
FIG. 85 is a top view of embodiments of the container with individual transparent slidable lids for multiple recesses.
Figure 86:
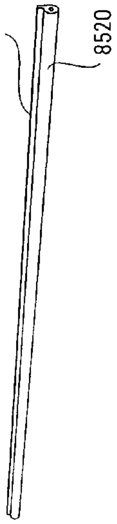
FIG. 86 is a perspective view of a spindle that may be used as part of an embodiment of a lock for the embodiments of the invention.

FIG. 83 illustrates embodiments of a locking mechanism 8300 that may be used with the container embodiments of FIGS. 81-84. See FIGS. 42-46 for more details on the operation of this locking mechanism. In the embodiment shown in FIGS. 81-84, a knob 8305 may be positioned as an integral part of the lid 8105. The locking mechanism of FIG. 83 may be positioned within a recessed area 8400 of the container, as illustrated in FIG. 84.

Figure 61:
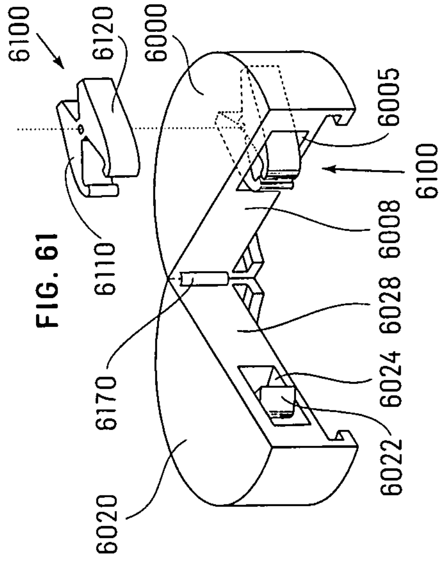
FIG. 61 is a perspective view of embodiments of the container cap of FIG. 60 in an open position.
Figure 62:
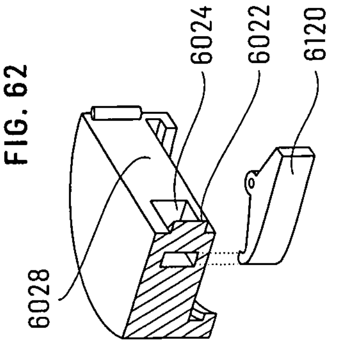
FIG. 62 is a perspective cross-sectioned view of a portion of the container cap of FIG. 61.
Figure 60:
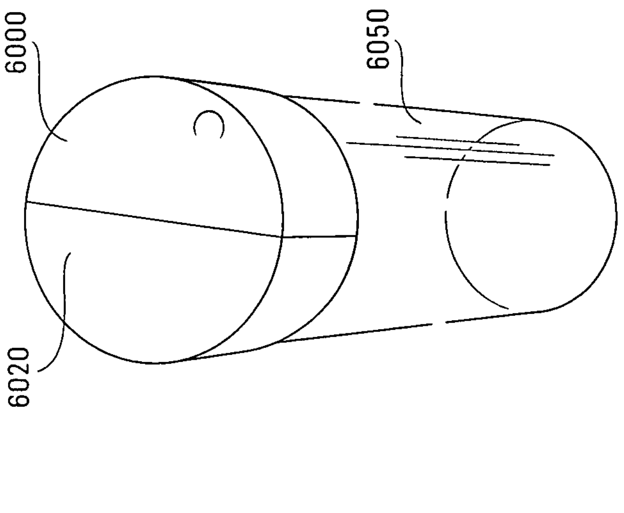
FIG. 60 is a perspective view of embodiments of the container and container cap.
Figure 67:
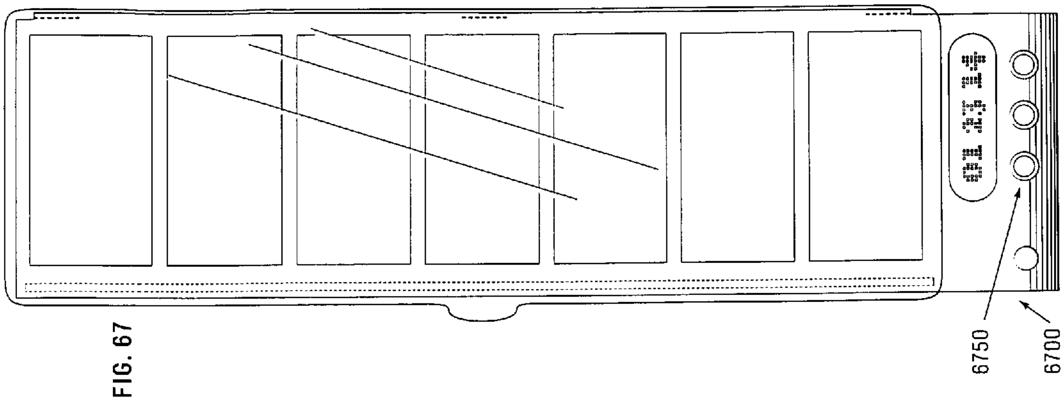
FIG. 67 is a top view of embodiments of a container consistent with the invention that may be used with the lids of FIGS. 65 and 66.
Figure 66:
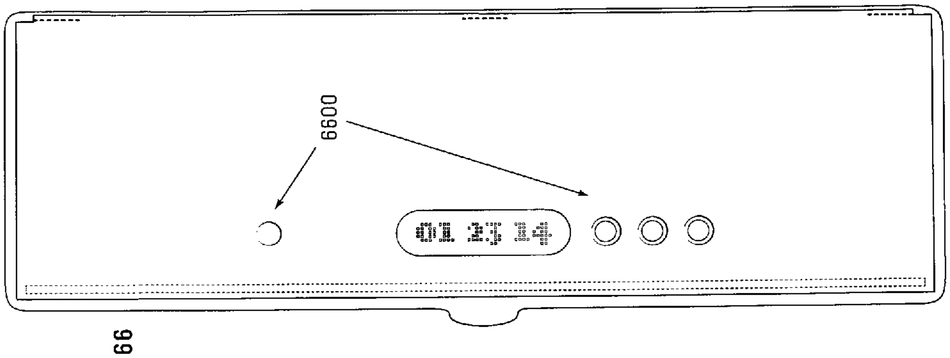
FIG. 66 is a top view of embodiments of a lid for a container consistent with the invention.
Figure 65:
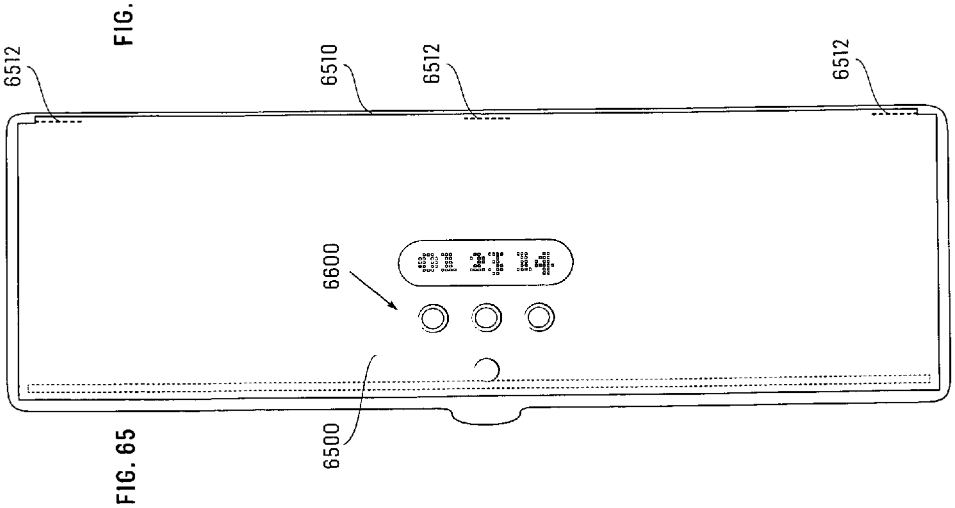
FIG. 65 is a top view of embodiments of a lid for a container consistent with the invention.
Figure 70:
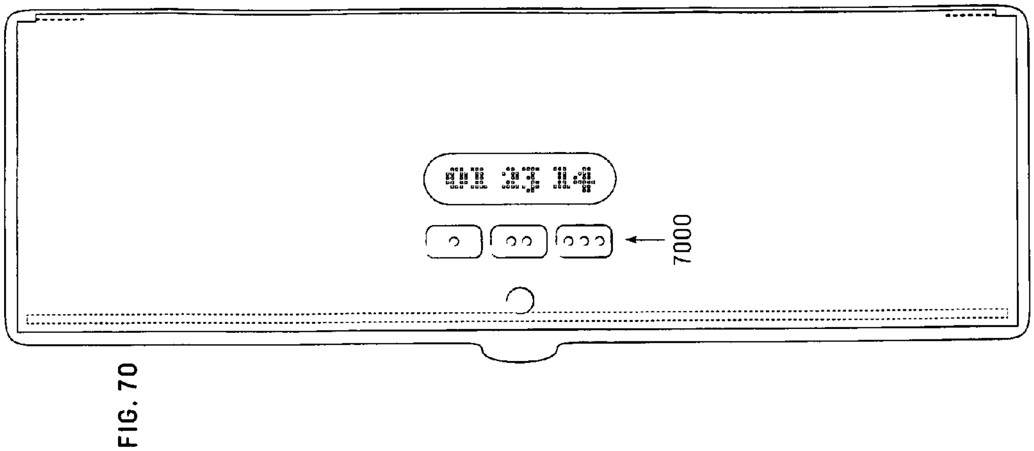
FIG. 70 is a top view of embodiments of a lid for a container consistent with the invention.
Figure 68:
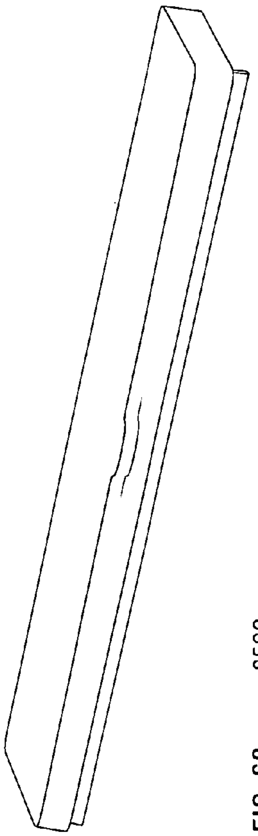
FIG. 68 is a perspective view of embodiments of the lid for a container consistent with the invention.
Figure 69:
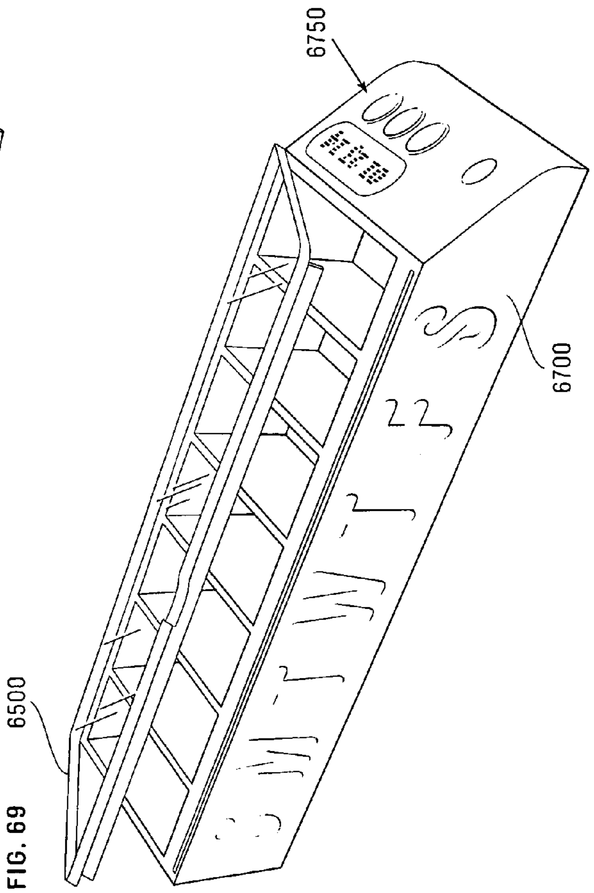
FIG. 69 is a perspective view of embodiments of a lid and a container consistent with the invention.

Note that the locking mechanism may take a variety of the different locking configurations, such as those shown in FIGS. 48, 61 and 73, to name a few.

Note that in other embodiments, the locking mechanism may be positioned within the lid and the knob 8305 may be positioned in a recess in an inner wall of the container.

FIGS. 85-89 illustrate a further embodiment of a container 8500 with individual compartments 8505, and an individual slidable lid 8510 for each of the compartments 8505.

Figure 87:
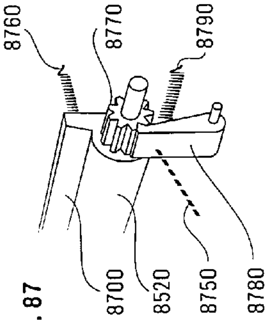
FIG. 87 is a perspective view of a gear wheel and pawl that may be used as part of an embodiment of a lock for the embodiments of the invention.

A further embodiment of a locking mechanism consistent with the invention is shown in FIGS. 87-89, comprising a spindle 8520, with a gear wheel 8770 thereon, and a pawl 8780. In embodiments, the spindle 8520 may be biased into a locking position. In embodiments, the mechanism for accomplishing the biasing may comprise a spring 8760 pulling on an end 8700 of the spindle 8520. In embodiments, the pawl 8780 may be biased by a spring 8790 to engage the teeth of the gear 8770 to prevent the spindle from rotating. As noted previously, the particular structure for accomplishing the biasing may take a variety of forms, and is not limiting on the invention.

Figure 88B:
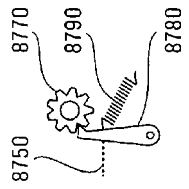
FIG. 88B is a side view of a locking mechanism that may be used to implement embodiments of the invention.
Figure 88A:
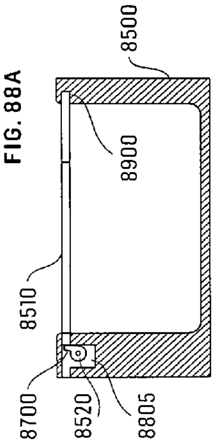
FIG. 88A is a cross-sectional side view of the container of FIG. 86 in a locked position.
Figure 89B:
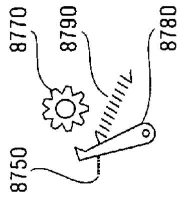
FIG. 89B is a side view of a locking mechanism that may be used to implement embodiments of the invention.
Figure 89A:
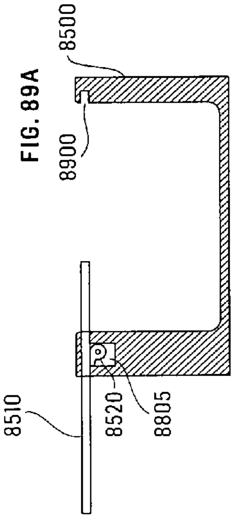
FIG. 89A is a cross-sectional side view of the container of FIG. 86 in an unlocked position.

FIG. 88A illustrates one of the lids 8510 slid across to cover its respective compartment 8505, with the end thereof fitting within a slot 8900. In embodiments, the spindle 8520 may be positioned within a recess 8805 in the container 8500. The spindle 8520 is shown in FIG. 88A in a locking position with an end 8700 thereof rotated against an end of the lid 8510. FIG. 89A illustrates one of the lids 8510 slid into an open position with the spindle 8520 rotated so that the end 8700 of the spindle fits in the recess 8805. FIG. 88B illustrates the pawl 8780 in a locked position. FIG. 89B illustrates the pawl 8780 in an unlocked position.

FIGS. 90-92 illustrate further embodiments of a container consistent with the invention. In embodiments, a lazy susan cylindrical container 9000 is shown with multiple compartments 9010. In embodiments, the lazy susan cylindrical container 9000 comprises an outer cylindrical wall 9015, and a cylindrical central wall 9020 that defines a central compartment 9025. The multiple compartments 9010 may be disposed between the outer cylindrical wall 9015 and the cylindrical central wall 9020. The cylindrical central wall 9020 may include a slot 9030 therein for each of the compartments 9010. In embodiments, the central compartment 9025 may comprise electronics for communication and a user interface.

FIG. 91 illustrates embodiments of a lid 9100 that may be used with the container embodiment of FIG. 90. In embodiments, the lid 9100 may comprise a top horizontal portion 9105, and a cylindrical outer wall 9120 configured to fit around the outer cylindrical wall 9015 of the container. In embodiments, the lid may comprise a central portion 9240 (see FIG. 92A) that fits within the space of the central compartment 9025 and includes the electronics and the user interface. In embodiments, the lid 9100 may comprise a cylindrical groove 9130 on an inner periphery of the cylindrical outer wall 9120 positioned to allow projections 9040 (shown in FIG. 92) of the container to ride therein. In embodiments, the projections 9040 may be cylindrical and may be configured to rotate to facilitate a rotation of the lid 9100. In other embodiments, the lid 9100 may comprise a central opening to accommodate the central compartment 9025 of the container 9000 that contains the electronics and the user interface.

FIG. 92 illustrates embodiments of a locking mechanism that may be used with embodiments of the invention. In embodiments, an interference block 9200 may be positioned in the central portion 9240 of the lid 9100 directed in a radial direction to move into and out of the slots 9030. In embodiments, the interference block 9200 may comprise a pin disposed within a slot cavity of the central portion 9240.

In embodiments, the lid 9100 may comprise a portion 9170 dimensioned to cover at least one of the compartments 9010. The portion 9170 has a tab that may be lifted to open or provide access to the contents, e.g., pills, held in the compartment 9010 therebelow, for that period. The portion 9170 may comprise a slot compartment 9175 horizontally positioned in the radial direction to receive the interference block/pin 9200 when it is slid through one of the slots 9030 in the inner wall 9020. In embodiments, the biasing mechanism may be configured so that the interference block/pin 9200 projects about 2/3 into the slot compartment 9175.

In embodiments, the interference block 9200 may be biased into a locking position with an end 9205 inserted through one of the slots 9030 into the slot compartment 9175. In embodiments, the biasing mechanism may comprise a spring 9215 positioned within the slot cavity of the central portion 9240. The spring 9215 may be connected at one end to an end of the slot cavity and connected at the other end to an end of the interference block 9200. In embodiments, the spring 9215 may normally have a length as shown in FIG. 92B. In embodiments, a shape memory material component 9225 may be positioned in parallel to the spring 9215 and may be connected at one end to an end of the slot cavity and connected at the other end to an end of the interference block 9200. When energized, the shape memory material component 9225 compresses the spring 9215 (shown in dashed lines above FIG. 92A) to move/retract the interference block 9200 out of the slot compartment 9175 in the lid and out of the slot 9030, to allow the lid to be rotated. In embodiments, the shape memory material component 9225 may comprise a wire. However, as noted previously, the shape memory material component 9225 may take any shape or position convenient to move the interference block into and/or out of a locking position within one of the slots 9030.

In embodiments shown in FIG. 91, the user interface may comprise buttons or other control elements 9050. In embodiments, the user interface may comprise a visual display 9060. In embodiments, the electronic control circuit may include a timer and/or may be programmed to obtain date and/or time data from a wireless or wired connection to a network, to control when the shape memory material component is energized and the interference block 9200 is retracted so that the lid may be rotated.

Figure 93:
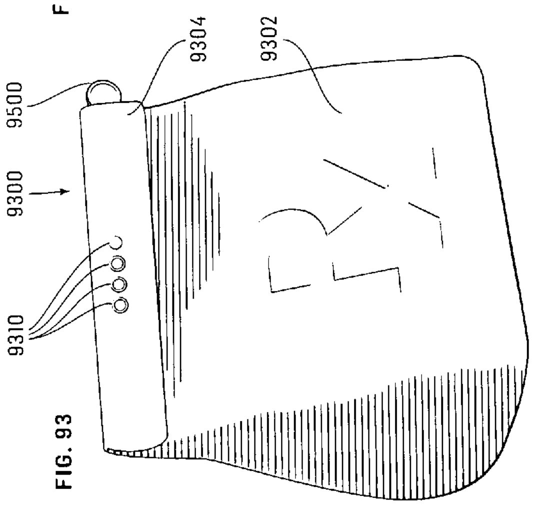
FIG. 93 is a perspective view of pouch embodiments of the container consistent with the invention with the flap closed.
Figure 94:
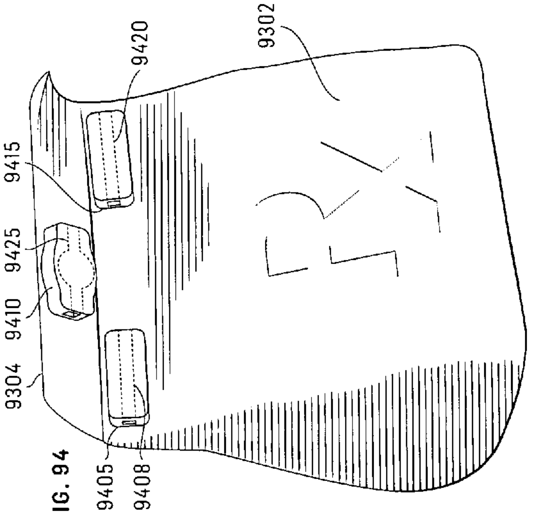
FIG. 94 is a perspective view of the pouch embodiments of the container of FIG. 93 with the flap open.
Figure 96:
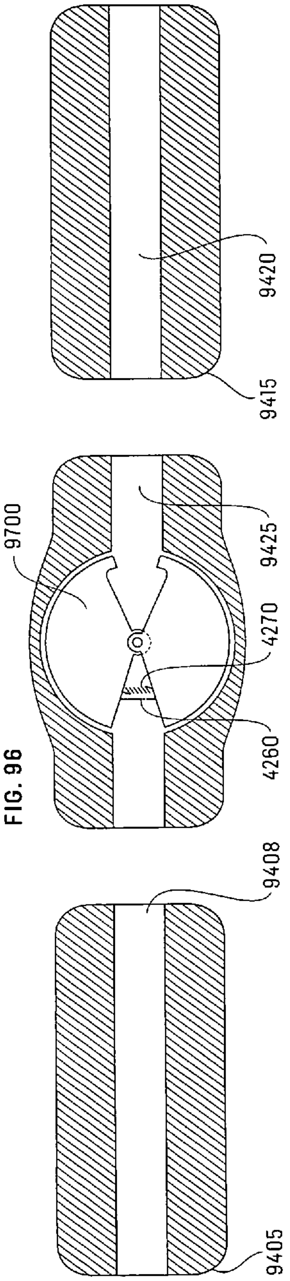
FIG. 96 is a cross-section view of embodiments of a locking mechanism that may be used with the container of FIG. 93.
Figure 97:
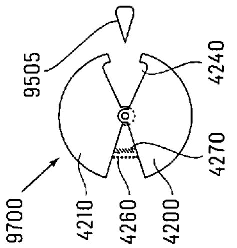
FIG. 97 is a side view of embodiments of a locking mechanism that may be used with the container of FIG. 93.
Figure 99:
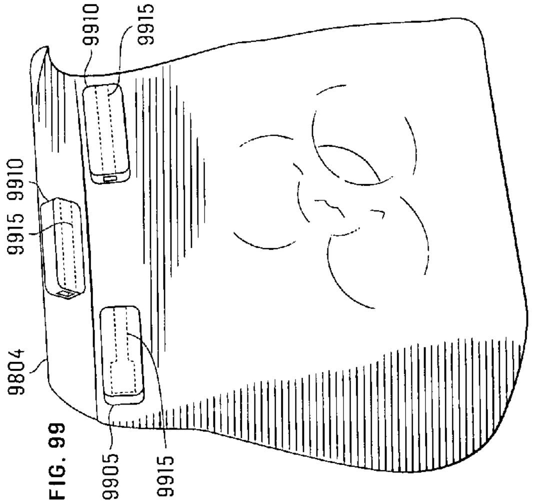
FIG. 99 is a perspective view of the pouch embodiments of the container of FIG. 98 with the flap open.
Figure 98:
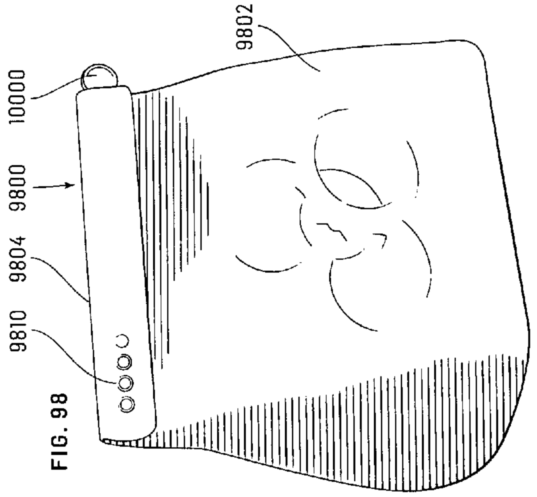
FIG. 98 is a perspective view of pouch embodiments of the container consistent with the invention with the flap closed.
Figure 100:
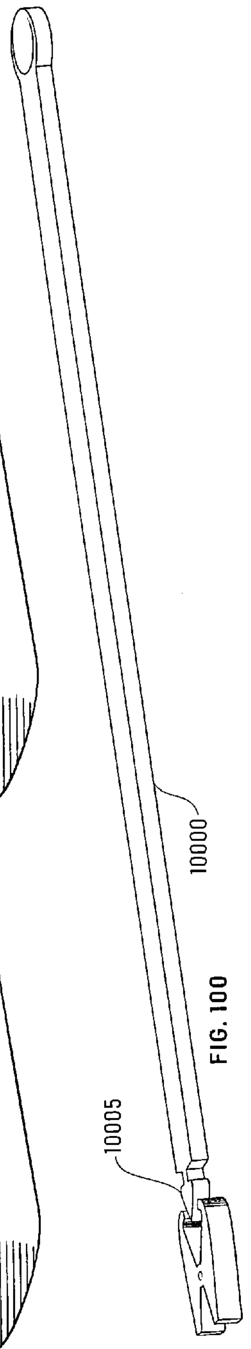
FIG. 100 is a perspective view of a bar that may be used in embodiments of a locking mechanism that may be used for the container of FIG. 98.
Figure 101:
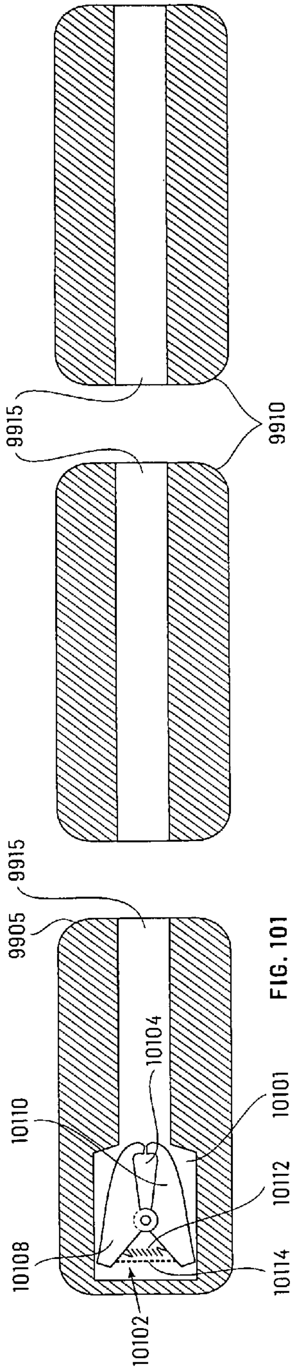
FIG. 101 is a cross-section view of embodiments of a locking mechanism that may be used with the container of FIG. 98.

FIGS. 93-94 illustrate embodiments of a pouch container 9300 consistent with the invention. The pouch container comprises a pouch 9302, with an opening at the top thereof that may be locked by a rigid or semi-rigid flap 9304. In embodiments, the flap 9304 may comprise control buttons 9310 for inputting a code to a locking mechanism 9410 attached to the inside or to the outside of the flap 9304. In embodiments, the locking mechanism 9410 may comprise a channel 9425 for receiving a bar 9500 therethrough. The pouch 9302 may comprise in embodiments a channel block 9405 with a channel 9408 therethrough that aligns with the channel 9425 of the locking mechanism 9410 when the flap is in a closed or down position, as shown in FIG. 93 and conceptually in FIG. 96. In embodiments, the pouch 9302 may further comprise a channel block 9415 with a channel 9420 therethrough that aligns on the other side with the channel 9425 of the locking mechanism 9410 when the flap is in the closed or down position. Details of embodiments of a lock 9700 that may be used in the locking mechanism 9410 are shown in FIG. 97. The operation of FIG. 97 has been previously described with respect to FIG. 42.

In embodiments, the bar 9500 may comprise an interference block 9505 extending from one side of the bar. In operation, when the bar 9500 is extended through the channel 9420, the channel 9425, and the channel 9408, the interference block 9505 on the side of the bar 9500 will move into the space 4240 in the lock 9700 and will be captured when the fractional disks 4210 and 4200 rotate into a closed position. In embodiments, the fractional disks may be triggered to close when the interference block is detected within the space 4240. In embodiments, the fractional disks 4210 and 4200 may be biased into a closed position by the spring 4270 or another mechanism. In embodiments, when the shape memory material component 4620 is energized via an electrical signal, the disks 4200 and 4210 are rotated open to allow the bar to be retracted.

Figure 95:
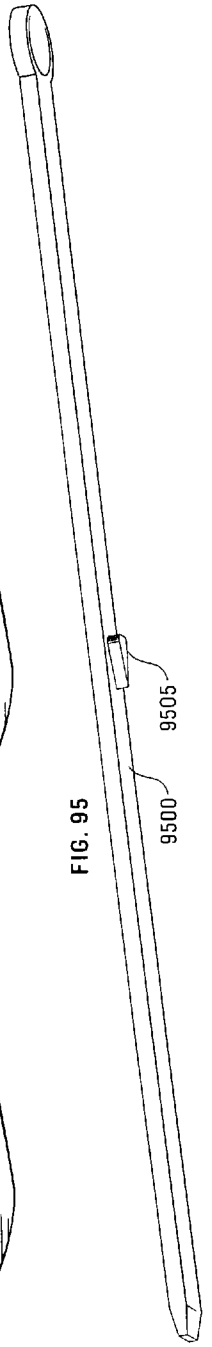
FIG. 95 is a perspective view of a bar that may be used in embodiments of a locking mechanism that may be used for the container of FIG. 93.

Note that in embodiments, the channel 9420 and at least a portion of channel 9425 may have a width to accommodate both the width of the bar 9500 and the width of the interference block 9505. Since the interference block will not pass through the channel 9408 and a portion of the channel 9425, this channel and portion of the channel 9425 need only have a width to accommodate the width of the bar 9500. Note that the bar in FIG. 95 and the locking mechanism and the channel blocks shown in FIG. 96 are approximately proportionate. The bar 9500 is not proportionate for FIGS. 93-94. Note that the channel openings may be beveled where appropriate to ease insert of the bar.

Note that in other embodiments, one or more of the channel blocks 9405 and 9415 may be attached to the inside or the outside of the flap 9304, and the locking mechanism 9410 may be attached to the upper part of the pouch 9302 and aligned so that the channels 9420, 9425 and 9408 align to receive the bar 9500 therethrough when the flap is closed.

Note that in embodiments a variety of different locks may be substituted for the lock of FIG. 97.

FIGS. 98-101 illustrate further embodiments of a pouch container 9800 consistent with the invention. The pouch container comprises a pouch 9802, with an opening at the top thereof that may be locked by a rigid or semi-rigid flap 9804. In embodiments, the pouch 9802 may comprise control buttons 9810 at the top thereof for inputting a code to a locking mechanism 9905 attached thereto just below the opening of the pouch. In embodiments, the locking mechanism 9905 may comprise a channel 9915 for receiving a bar 10000 therethrough. The flap 9804 may comprise in embodiments one or more channel blocks 9910 with a channel 9915 therethrough that aligns with the channel 9915 of the locking mechanism 9905 when the flap is in a closed or down position, as shown conceptually in FIG. 101.

In embodiments, a lock 10102 may be positioned within a recess 10101 at one end of the channel 9915. In embodiments, the lock 10102 may have the same or a similar design as FIG. 97 or FIG. 57. A capture volume 10104 may be formed by two clip pieces 10108 and 10110 of the lock 10102. The capture volume 10104 may be aligned to receive an interference block 10005 positioned at one end of a bar 10000. The lock may comprise, in embodiments, a spring 10112 to bias the clip pieces into a locked position, and a shape memory material component 10114 for opening the lock under electronic control.

Note that in other embodiments, the locking mechanism 9410 may be attached to the flap 9804 and aligned so that the channels 9915 may receive the bar 10000 therethrough.

Figure 57:
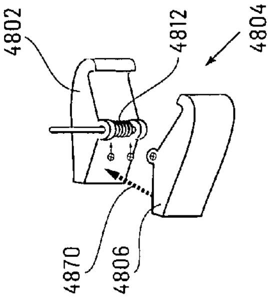
FIG. 57 is a perspective view of embodiments of a locking mechanism that may be used with the container cap of FIG. 53.
Figure 58:
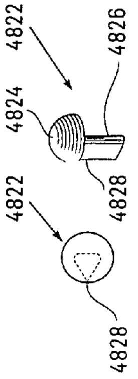
FIG. 58 is a perspective view of embodiments of a knob that may be used with embodiments of the container cap of FIG. 53.
Figure 59:
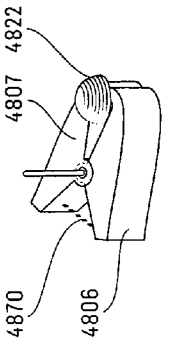
FIG. 59 is a perspective view of embodiments of a knob and a locking mechanism that may be used with embodiments of the container cap of FIG. 53.
Figure 55:
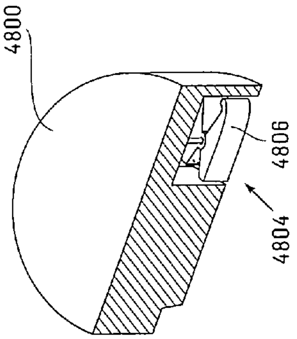
FIG. 55 is a perspective cross-sectional view of embodiments of a top portion of the container cap of FIG. 53.
Figure 56:
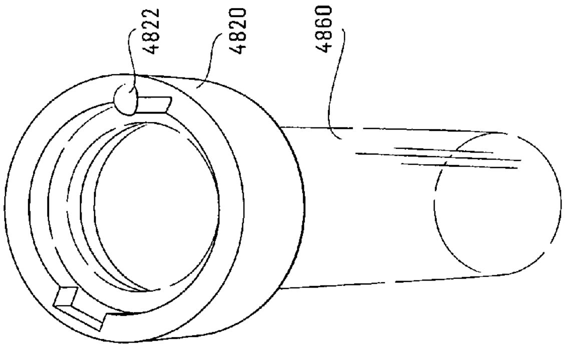
FIG. 56 is a perspective view of the bottom portion of the container cap of FIG. 53.
Figure 53:
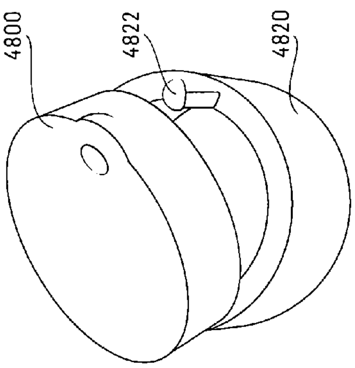
FIG. 53 is a perspective view of further embodiments of a container cap consistent with the invention.
Figure 54:
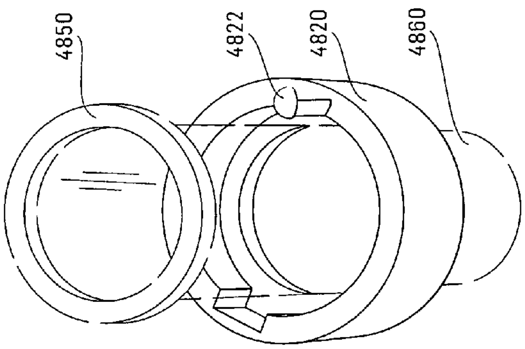
FIG. 54 is a perspective view of embodiments of a bottom portion of the container cap of FIG. 53 with an exploded view of a lip of a container illustrated.
Figure 63:
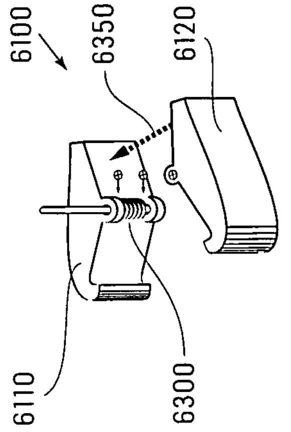
FIG. 63 is a perspective view of a locking mechanism that may be used with embodiments of the container cap of FIG. 60 shown in an open position.
Figure 64:
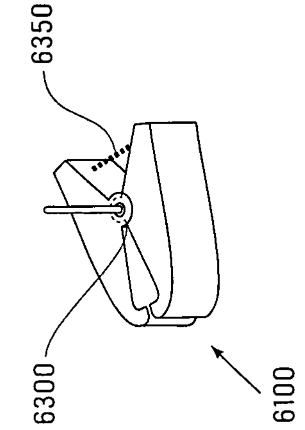
FIG. 64 is a perspective view of a locking mechanism that may be used with embodiments of the container cap of FIG. 60 shown in a locked position.

Note that in embodiments a variety of different locks may be substituted for the locks of FIGS. 97 and 57.

In embodiments, instead of a flap or in addition to a flap, a zipper may be used to seal the top of the pouch. In embodiments, any of the locking mechanisms described may be positioned at one end of the zipper, to lock a handle of the zipper therein.

In embodiments of the container cap, consistent with FIGS. 10-16,

- wherein the cap housing comprises a first portion and a second portion, with a first lateral track formed in the first portion of the cap housing with a slot at one end thereof, and a second lateral track formed in the second portion of the cap housing, with the second lateral track in parallel and adjacency to the first lateral track, and
- wherein the interference block comprises a lateral projection at one end thereof that slides within the first lateral track and the fits within the slot of the first lateral track when the shape-memory material component has the first length and/or shape, and
- wherein the interference block comprises a downward projection at another end thereof that slides within the second lateral track.

In embodiments of the container cap consistent with FIGS. 10-16,

- wherein the cap housing comprises a key pad for controlling the electrical logic component supplying electrical current from the electrical current source to the shape memory material component to cause the shape memory material component to change between the first length and/or shape and the second length and/or shape.

In embodiments of the container cap consistent with FIGS. 10-16,

- wherein the electrical circuit comprises logic to allow the interference block to take the second non-interfering position only during specified hours of a day or only a specified number of times per day or only one or more specified days of the week.

In embodiments of the container cap, consistent with FIGS. 10-16, the container cap further comprises:

- a network communication device comprising a receiver disposed in the portable housing for receiving control signals from a communication network to control the electrical circuit to supply electrical current from the electrical current source to the shape memory material component to cause the shape memory material component to change between the first length and/or shape and the second length and/or shape, and
- wherein the electrical circuit comprises logic to control supply of the electrical current from the electrical current source to the shape memory material component based at least in part on the control signals.

In embodiments of the container cap, wherein the network communication device comprises a cellular telephone circuit or a transceiver.

In embodiments the container cap may further comprise:

- a network communication device comprising a receiver and a transmitter disposed in the portable housing for receiving and sending voice signals over a network.

In embodiments of the container cap:

- wherein the electrical circuit comprises logic for generating for data transmission on removal of the cap housing from the open end of the container,
- wherein the network communication device is configured to transmit the data on the removal of the cap housing from the open end of the container.

In embodiments of the container cap:

wherein the cap housing further comprises an electronic display screen, wherein the electrical circuit further comprises an electronic memory, and wherein the electrical circuit is configured to record data on removal of the cap housing from the open end of the container in the electronic memory and display data based on the removal data on the electronic display screen.

In embodiments the container cap may further comprise a spring positioned to hold the interference block in the first interfering position.

In embodiments of the container cap wherein the power source comprises an electrical current source selected from the group of a battery, a kinetic charger, and an induction device.

In embodiments of the container cap wherein the electrical circuit is configured to limit a level of the electrical current supplied to the shape memory material component to a predetermined electrical current range.

In embodiments the container cap may further comprise:

a network communication device disposed in the cap housing; and a tracking element comprising one or more selected from the group of a GPS circuit and a cellular telephone circuit for location determination and transmission of location data over a communications network via the network communication device.

In embodiments of the container cap wherein the shape-memory material component is selected from the group of a shape-memory alloy component, an electroactive polymer, and a twisted carbon nanotube.

In embodiments of the container cap, consistent with FIG. 21, wherein the cap housing comprises a first portion and a second portion, with opposing parallel surfaces, with a projection extending from the parallel surface of the first portion, with a side extension that extends substantially parallel to the parallel surface from the projection, wherein the second portion comprises a recess in which the projection may fit when the first and second portions are fitted together, wherein the recess in the second portion comprises an interference block with a side projection 2052, wherein the interference block is laterally slidable within the recess 2040 in a direction that is parallel to the parallel surface, so that the side projection of the interference block fits in registration with the side extension of the projection of the first portion within the recess when the shape-memory material component has the first length and/or shape so that the interference block is in a first interfering position.

Figure 26A:
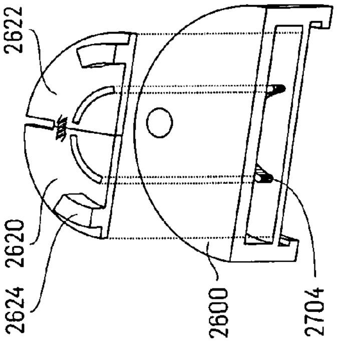
FIG. 26A is an exploded perspective view of a first portion of another embodiment of the container cap.
Figure 26B:
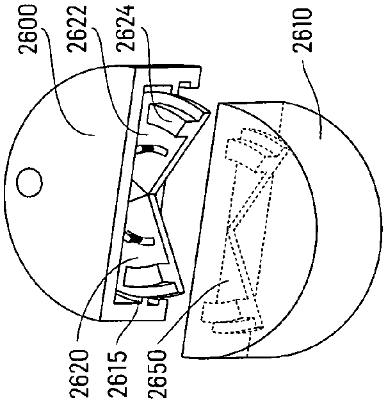
FIG. 26B is a perspective view of a separated first and second portions of the container cap of FIG. 26A.

In embodiments of the container cap, consistent with FIG. 26:

wherein the cap housing comprises a first portion and a second portion, with opposing parallel surfaces, wherein the interference block comprises two pieces on a same plane positioned to be rotatable around a track within the first portion, wherein the second portion comprises a track on the same plane as the track in the first portion and positioned to receive at least a portion of the two pieces therein when the pieces are rotated away from each other;

wherein the shape memory material component is connected to opposing sides of the two pieces, wherein when the shape memory material component has the first length and/or shape, the two pieces are rotated apart into the track in the second portion to thereby impede removal of the cap housing from the open end of the container, and when the shape memory material component has the second length and/or shape, the two pieces are not rotated into the second portion thereby not interfering with removal of the cap housing from the open end of the container.

In embodiments of the container cap consistent with FIG. 26, wherein each of the two pieces comprises a fractional portion of a disk that is positioned to slide on the track in the first portion.

In embodiments of the container cap consistent with FIG. 31, wherein the container cap comprises a recess disposed to extend from inside the container cap to an opening in a side of the container cap, wherein the interference block is positioned within the recess, and slidable within the recess to project through the opening into a recess on a side of the container, to thereby be in an interfering position, wherein the shape memory material component is connected at one end thereof within the recess in the container cap, and connected at another end thereof to the interference block, wherein when the shape memory material component has the first length and/or shape, an end of the interference block is extended into the recess into the container, and when the shape memory material component has the second length and/or shape, the interference block is entirely within the recess in the container cap and in the non-interfering position.

In embodiments of the container cap consistent with FIG. 31, the container cap may further comprise a hinge connecting one end of the container cap to an edge of the opening in the container.

In embodiments of the container cap consistent with prong embodiments, wherein the interference block comprises two pieces, with each piece comprising at least one end, wherein the shape memory material component is positioned between the two pieces, so that when the shape memory material component has the first length and/or shape, the at least one end for each of the pieces is extended into a respective recess in a side of the open end of the container, and when the shape memory material component has the second length and/or shape, the at least one end for each of the pieces is not extended into its respective recess in the side of the open end of the container.

In embodiments of the container cap consistent with FIGS. 41-47, wherein the cap housing comprises a first portion and a second portion, wherein the interference block comprises two pieces on a same plane positioned to be rotatable around a track within the first portion, wherein each of the two pieces comprises a circumferential projection at one end thereof, with the projections positioned to oppose each other and to form a boundary of an opening defined within the two pieces adjacent the one end, wherein the second portion comprises a track on the same plane as the track in the first portion and positioned to receive at least a portion of the two pieces therein that have the circumferential projections thereon, wherein the second portion comprises a projection positioned thereon to fit within the opening defined within the two pieces, wherein the shape memory material component is connected to opposing sides of the two pieces, wherein when the shape memory material component has the first length and/or shape, the two pieces are rotated so that the circumferential projections are in adjacency or touch to thereby trap the projection on the second portion with the opening to thereby impede removal of the cap housing from the open end of the container, and when the shape memory material component has the second length and/or shape, the two pieces are rotated to move the circumferential projections away from each other to no longer trap the projection on the second portion and allow removal of the cap housing from the open end of the container.

In embodiments of the container cap consistent with FIGS. 41-47, wherein each of the two pieces comprises a fractional portion of a disk that is positioned to slide on the track in the first portion.

In embodiments of the container cap consistent with FIGS. 41-47, wherein the two pieces are biased so that the circumferential projections are in adjacency or touch to thereby trap the projection on the second portion with the opening.

In embodiments of the container cap consistent with FIGS. 48-52, wherein the cap housing comprises a first portion and a second portion, wherein the interference block comprises a first clip piece with an end thereof biased toward a second clip piece to form a clip connected to the first portion, wherein the second portion comprises a knob extending from a surface of the second portion, with the knob having indents formed below a top portion of the knob, and with the knob positioned in alignment with the clip so that clip fits around the knob when in a locked position and prevents the first portion from being separated from the second portion, and wherein the shape memory material component is connected between the first clip piece and the second piece so that when the shape memory material component has the first length and/or shape, the interference block is disposed around the knob in the indents to prevent separation of the first portion from the second portion, and when the shape memory material component has the second length and/or shape, the interference block allows separation of the first portion from the second portion.

In embodiments of the container cap consistent with FIGS. 48-52, the container cap may further comprise a spring for biasing the end of the clip piece toward the end of a wall of the first portion.

In embodiments of the container cap consistent with FIGS. 48-52, wherein the end of the second clip piece comprises a wall of the first portion.

In embodiments of the container cap consistent with FIGS. 48-52, wherein the clip is positioned perpendicular and toward the opening of the container.

In embodiments of the container cap consistent with FIGS. 48-52, wherein the clip is positioned in parallel to the opening of the container.

In embodiments of the container cap consistent with FIGS. 60-64, wherein the cap housing comprises a first portion and a second portion with opposing parallel surfaces, wherein the interference block comprises a first clip piece with an end thereof biased toward an end of a second clip piece to form a clip connected to the first portion, with the clip positioned within a recess formed in the parallel surface of the first portion, but extending partially from the surface of the parallel surface of the first portion, wherein the second portion comprises a projection extending across a recess formed in the parallel surface of the second portion formed, wherein the clip is positioned so that the end of the first clip piece and the end of the second clip piece extend into the recess on either side of the projection to fit around and behind the projection in the second portion when in a locked position and prevent the first portion from being separated from the second portion, and wherein the shape memory material component is connected between the first clip piece and the second piece so that when the shape memory material component has the first length and/or shape, the ends of the first and second clip pieces extend around and behind the projection in the second portion to prevent separation of the first portion from the second portion, and when the shape memory material component has the second length and/or shape, the ends of the first and second clip pieces are moved apart to allow separation of the first portion from the second portion.

In embodiments of the container cap consistent with FIGS. 65-80, wherein the cap housing comprises a hinge at a first side thereof to hinge the cap housing to a first side of the open end of the container, wherein the interference block is positioned at a second side of the cap housing that is opposite to the side with the hinge.

In embodiments of the container cap consistent with FIGS. 65-80, wherein the interference block comprises a clip, wherein a second side of the open end of the container opposite to the first end comprises a knob extending from a surface of the second side of the open end of the container, with the knob having at least one indent formed below a top portion of the knob, and with the knob positioned in alignment with the clip so that clip fits around the knob into the indent when in a locked position and prevents the cap housing from being separated from the open end of the container, and wherein the shape memory material component is connected within the clip so that when the shape memory material component has the first length and/or shape, the interference block is disposed to around the knob in the at least one indent to prevent separation of the cap housing from the open end of the container, and when the shape memory material component has the second length and/or shape, the interference block allows separation of the cap housing from the open end of the container.

In embodiments of the container cap consistent with FIGS. 65-80, wherein the interference block is slidable between a first locking position and a second unlocked position, wherein a second side of the open end of the container opposite to the first end comprises a knob extending from a surface of the second side of the open end of the container, with the knob having at least one indent formed below a top portion of the knob, and with the knob positioned so that the interference block may be slid so that a portion thereof fits in registration with the indent in the knob when in a locked position to prevent the container cap from being separated from the second side of the container, and wherein the shape memory material component is connected to one end of the interference block so that when the shape memory material component has the first length and/or shape, the interference block is positioned to fit in registration with the indent in the knob for the locked position to prevent separation of the cap housing from the open end of the container, and when the shape memory material component has the second length and/or shape, the interference block is no longer in registration with the indent in the knob thereby allowing separation of the cap housing from the open end of the container.

In embodiments of the container cap consistent with FIGS. 65-80, wherein the interference block is biased into the locked position.

In embodiment, configurations of the design may use Multiple Memory Materials (MMM) also called Multiple Memory Shape Memory Alloys, which allow two "strong" undeformed positions that depend on temperature and can be controlled to take these positions based at least in part on the heat applied. Thus, the level of the current or light or other energy applied to the alloy would control the different positions. Accordingly, in embodiments the same Multiple Memory Shape Memory Alloy wire may pull left or right depending on the temperature. Thus, such embodiments with a multiple memory shape alloy wire may be used to reduce the number of shape memory wires required. In embodiments, such a configuration may be used without a spring to save production costs by having the lower temperature push the lock closed and the higher temp opening it. Thus, as shape memory wire cools, the default locked position is taken.

In embodiments using the shape memory alloy, it may be made part of a switch. Because the alloy conducts electricity, it may be placed in the circuit so that when it reaches the correct shape after heating, it breaks the circuit.

In embodiments, a two wire shape memory material component may be used, one of the wires moves the interference block into an unlock position, and the other wire may be configured to move the interference block into a locking position. In some embodiments, a spring will be used to hold the interference block in a locking position when the power for heating is shut off. In some embodiments, no spring will be used.

In embodiments, the keypads used may comprise thinfilm keypads, and/or printable circuits such as graphene-based printing.

It is important to note that the construction and arrangement shown in the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, manufacturing processes, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to exemplary embodiments. Other substitutions, modifications, changes and omissions may also be made in the design, operating conditions and arrangement of the various exemplary embodiments without departing from the scope of the present disclosure.

We claim:

1. A tracking device, comprising:

a portable housing with a locking mechanism;

a band in cooperation with the portable housing and configured to be latched about a wrist or ankle of a person;

a tampering detection device configured in relation to the housing and/or the band to detect tampering with the band or unauthorized release;

the locking mechanism comprising:

a power source;

a latch configured to latch at least one end of the band within the housing;

a shape memory material component connected to the latch;

an electrical circuit for controlling the power source to heat the shape memory material component to cause the shape memory material component to change from a first length and/or first shape to a second length and/or second shape during supply of power;

wherein when the shape memory material component has the first length and/or shape, the latch prevents release of the one end of the band, and when the shape memory material component has the second length and/or shape, the latch is moved to allow release of the one end of the band;

wherein the electrical circuit is configured to control heating of the shape memory material component based on one or more criteria;

a timer component associated with the electrical circuit to cause supply of the power for a predetermined period of time when the electrical circuit component is triggered to heat the shape memory material component;

a two-way network communication device disposed in cooperation with the portable housing;

a tracking element for facilitating location determination and transmission of a location signal; and a tampering signal generation circuit configured to generate a tampering signal for transmission via the two-way communication device when tampering is detected by the tampering detection device.

2. The tracking device as defined in claim 1, wherein the shape memory material component is a shape memory material alloy.

3. The tracking device as defined in claim 1, wherein the shape memory material component is an electroactive polymer.

4. The tracking device as defined in claim 1, wherein the shape memory material component is a twisted carbon nanotube.

5. The tracking device as defined in claim 1, wherein the shape memory material component comprises a shape memory material wire.

6. The tracking device as defined in claim 1, further comprising an audible alarm device to generate an audible alarm signal when tampering is detected by the tampering detection device.

7. The tracking device as defined in claim 1, further comprising a panic button on the portable housing connected to the two-way communication device to generate a panic signal for transmission via the two-way communication device.

8. The tracking device as defined in claim 1, further comprising a stress detector disposed in the portable housing and/or the band and configured:

to measure one or more biological indicators, and to generate a signal for transmission providing a stress alert and location data via the two-way communication device when stress based on measurements of one or more of the one or more biological indicators is determined.

9. The tracking device as defined in claim 1, wherein the latch comprises an interference block.

10. The tracking device defined in claim 1, wherein the latch comprises an interference block that pivots on an axis between a first position that functions to lock the one end of the band within the housing, and a second position that allows the band to be released from the portable housing.

11. The tracking device as defined in claim 1, wherein the electrical logic component is configured to limit a level of the electrical current supplied to the shape memory material component to a predetermined current range.

12. The tracking device as defined in claim 1, wherein when the electrical circuit supplies current from the electrical current source to the shape memory material component, the shape memory material component changes from the first length and the first shape to the second length and the second shape.

13. The tracking device as defined in claim 1, wherein the latch comprises a lever attached directly or indirectly to an interference block, and wherein when the shape memory material component takes the second length and/or shape, the lever is configured to move the interference block out of interference with the band so that the band may be released from the portable housing.

14. The tracking device as defined in claim 1, wherein the latch comprises an interference block configured to slide between a first interfering position and a second non-interfering position when the length and/or the shape of the shape memory material component changes.

15. The tracking device as defined in claim 10, further comprising a spring positioned to hold the interference block in the first interfering position.

16. The tracking device as defined in claim 1, wherein the power source comprises an electrical current source selected from the group of a battery, a kinetic charger, and an induction device.

17. The tracking device as defined in claim 1, wherein the tracking element comprises one or more selected from the group of a GPS circuit and a cellular telephone circuit.

* * * * *